US008637091B2

(12) United States Patent  
Pluta et al.

(10) Patent No.: US 8,637,091 B2
(45) Date of Patent: Jan. 28, 2014

(54) COMPOSITIONS COMPRISING PARTICLES RESULTING FROM PROCESSING IN A SLURRY MIX

(75) Inventors: Richard C. Pluta, Towaco, NJ (US); John T. Mosko, Perth Amboy, NJ (US)

(73) Assignee: Tessenderlokerley Inc, Phoenix, AZ (US)

( * ) Notice: Subject to any disclaimer, the term of this patent is extended or adjusted under 35 U.S.C. 154(b) by 1089 days.

(21) Appl. No.: 11/380,639

(22) Filed: Apr. 27, 2006

(65) Prior Publication Data

US 2006/0252649 A1   Nov. 9, 2006

Related U.S. Application Data

(60) Provisional application No. 60/594,745, filed on May 3, 2005, provisional application No. 60/594,918, filed on May 18, 2005.

(51) Int. Cl.
*A01N 59/06* (2006.01)
*A01N 25/26* (2006.01)

(52) U.S. Cl.
USPC ............................ 424/684; 424/683; 504/100

(58) Field of Classification Search
None
See application file for complete search history.

(56) References Cited

U.S. PATENT DOCUMENTS

| 2,373,911 | A | * | 4/1945 | Pike | 423/161 |
| 3,120,445 | A | | 4/1964 | Aluisi | 106/286 |
| 3,159,536 | A | | 12/1964 | Marotta | 167/42 |
| 3,231,365 | A | | 1/1966 | Wahlberg | 71/64 |
| 3,490,932 | A | | 1/1970 | Smith et al. | 106/157 |
| 3,586,523 | A | * | 6/1971 | Fanselow et al. | 106/486 |
| 3,914,469 | A | | 10/1975 | Delano et al. | 427/164 |
| 3,956,487 | A | * | 5/1976 | Hata et al. | 514/62 |
| 4,010,278 | A | | 3/1977 | Adams | 424/309 |
| 4,192,691 | A | | 3/1980 | Armanini | |
| 4,211,785 | A | | 7/1980 | Nakagawa et al. | 424/272 |
| 4,371,626 | A | * | 2/1983 | Hentz | 501/145 |
| 4,509,987 | A | | 4/1985 | Farrar et al. | 106/308 Q |
| 4,738,726 | A | | 4/1988 | Pratt et al. | |
| 4,781,298 | A | | 11/1988 | Hemstock et al. | |
| 4,804,403 | A | * | 2/1989 | Moore | 71/28 |
| 5,122,518 | A | | 6/1992 | Vrba | 514/63 |
| 5,171,349 | A | | 12/1992 | Vetanovetz et al. | 71/29 |
| 5,252,118 | A | | 10/1993 | Brown | 71/23 |
| 5,311,997 | A | | 5/1994 | Gantt et al. | |
| 5,395,418 | A | | 3/1995 | Vetanovetz | 71/29 |
| 5,521,144 | A | * | 5/1996 | Farr et al. | 504/215 |
| 5,597,400 | A | | 1/1997 | Nonomura et al. | 71/28 |
| 5,611,691 | A | | 3/1997 | Poulain | |
| 5,690,897 | A | * | 11/1997 | Drummond | 423/173 |
| 5,741,355 | A | | 4/1998 | Yamamoto et al. | |
| 5,891,235 | A | * | 4/1999 | Suzuki et al. | 106/483 |
| 5,908,708 | A | | 6/1999 | Sekutowski et al. | |
| 6,045,914 | A | | 4/2000 | Sullivan et al. | |
| 6,060,521 | A | | 5/2000 | Sekutowski et al. | |
| 6,069,112 | A | | 5/2000 | Glenn et al. | |
| 6,110,867 | A | | 8/2000 | Glenn et al. | |
| 6,156,327 | A | | 12/2000 | Sekutowski et al. | |
| 6,235,683 | B1 | | 5/2001 | Glenn et al. | |
| 6,378,703 | B1 | | 4/2002 | Mathur et al. | |
| 6,464,995 | B1 | | 10/2002 | Sekutowski et al. | |
| 6,514,512 | B1 | | 2/2003 | Puterka et al. | |
| 6,631,001 | B2 | * | 10/2003 | Kuiseko | 356/456 |
| 6,652,642 | B2 | * | 11/2003 | Sare et al. | 106/486 |
| 6,877,275 | B2 | * | 4/2005 | Glenn et al. | 47/58.1 SC |
| 7,018,643 | B2 | | 3/2006 | Puterka et al. | |
| 2004/0146617 | A1 | | 7/2004 | Schrader | |

FOREIGN PATENT DOCUMENTS

JP    58-65201    4/1983

OTHER PUBLICATIONS

Carrado et al. "Synthetic Clay Minerals and Purification of Natural Clays" in Handbook of clay science. Bergaya et al Eds. Elsivier: Netherlands, 2006; p. 130.*
Rosen Surfactants and interfacial phenomena. Wiley: New Jersy, 2004; p. 345.*
Meda et al., Brazilian Archives of Biology and Technology, 45(2), 219-222, 2002. Dolomite Lime's reaction . . . .*
Hammer et al. "Limestone" in The potter's dictionary of materials and techniques. University of Pennsylvania Press: Philadelphia; 2004. p. 213).*
MSDS sheet of Atomite®, prepared on Jul. 27, 1982, accessed on Feb. 10, 2010.*
Meda et al., Brazilian Archives of Biology and Technology, 45(2), 219-222, 2002. Dolomite Lime's reaction. . . .*
Hammer et al. "Limestone" in the potter's dictionary of materials and techniques. University of Pennsylvania Press: Philadelphia; 2004. p. 213.*
MSDS sheet of Atomite ®.*
Sir Arthur Hort, Theophrastus: Enquiry into Plants and Minor Works on Odours and Weather Signs. G.P. Putnam's Sons, New York, (1916), pp. 404-409.
D. M. Glenn et al., "Hydrophobic Particle Films: A New Paradigm for Suppression of Arthropod Pests and Plant Diseases," *Journal of Economic Entomology*, vol. 92(4) (1999), pp. 759-71.
Antoine Abou-Khaled et al., "Effects of Kaolinite as a Reflective Antitranspirant on Leaf Temperature, Transpiration, Photosynthesis, and Water-Use Efficiency," *Water Resources Research*, vol. 6, No. 1 (1970), pp. 280-89.

(Continued)

*Primary Examiner* — David J Blanchard
*Assistant Examiner* — Tigabu Kassa
(74) *Attorney, Agent, or Firm* — Christopher G. Hayden

(57) ABSTRACT

The present invention provides a composition comprising functional mineral that is substantially free of crystalline silica. The agricultural particle film composition may be applied to horticultural plants and animals.

37 Claims, 6 Drawing Sheets

(56) References Cited

OTHER PUBLICATIONS

P. Alexander et al., "Inert dust insecticides. Part I. Mechanism of action." *The Annals of Applied Biology*, vol. 31 (1944), pp. 143-49.
P. Alexander et al., "Inert dust insecticides. Part II. The nature of effective dusts." *The Annals of Applied Biology*, vol. 31 (1944), pp. 150-56.
P. Alexander et al., "Inert dust insecticides. Part III. The effect of dusts on stored products pests other than *Calandra granaria*." *The Annals of Applied Biology*, vol. 31 (1944), pp. 156-59.
M. W. Baradas et al., "Reflectant Induced Modification of Soybean Canopy Radiation Balance. IV. Leaf and Canopy Temperature." *Agronomy Journal*, vol. 68 (1976), pp. 843-48.
M. W. Baradas et al., "Reflectant Induced Modification of Soybean Canopy Radiation balance. V. Longwave Radiation Balance." *Agronomy Journal*, vol. 68 (1976), pp. 848-52.
H. K. Berry, "Aluminum Silicate," in Pigment Handbook. Volume 1. Properties and Economics. Peter A. Lewis, Ed., Second Edition, John Wiley & Sons, New York, 1988, 183-95.
J. A. Bunce, "Nonstomatal inhibition of photosynthesis by water stress. Reduction in photosynthesis at high transpiration rate without stomatal closure in field-grown tomato." *Photosynthesis Research*, vol. 18 (1988), pp. 357-62.
R. E. Byers et al., "Reduction in Russetting of 'Golden Delicious' Apples with 2,4,5-TP and Other Compounds", *HortScience*, vol. 18 (1983), pp. 63-65.
R. E. Byers et al., 'Stayman' Fruit Cracking as Affected by Surfactants, Plant Growth Regulators, and Other Chemicals, J. Amer. Soc. Hort. Sci. 115(3) (1990), pp. 405-11.
A. Chahi et al., "The Use of Surfactant for Clay Dispersion in Organic Matter-Rich Soil: Preliminary Examination," *Soil Science*, vol. 161(11) ((1996), pp. 761-69.
James d'A. Clark, Pulp Technology and Treatment for Paper. Second Edition. "31. Filling and bonding materials." Miller Freeman Publications, Inc., San Francisco, 1985, pp. 31.1-31.6.
R. A. Cline et al., "Effects of Boron and Calcium Sprays and of Mulch on Cracking of Italian Prune," *Canadian Journal of Plant Science*, vol. 53 (1973), pp. 827-31.
P. C. Doraiswamy et al., "Reflectant Induced Modification of Soybean Canopy Radiation Balance. I. Preliminary Tests with a Kaolinite Reflectant." *Agronomy Journal*, vol. 66 (1974), pp. 224-28.
B. F. Driggers, "Experiments with Talc and Other Dusts Used Against Recently Hatched Larvae of the Oriental and Codling Moths," *Journal of Economic Entomology*, vol. 22 (1929), pp. 327-34.
E. F. Durner et al., "Peach Pistil Growth Inhibition and Subsequent Bloom Delay by Midwinter Bud Whitewashing," *HortScience* 25(10) (1990), pp. 1222-24.
E. F. Durner et al., "Interactions of Ethephon, Whitewashing, and Dormant Oil on Peach Pistil Growth, Hardiness, and Yield," *HortScience* 27(2) (1992), pp. 104-5.
A. S. Dukhin et al., "Surfactant Titration of Kaolin Slurries using ζ-Potential Probe," Dispersion Technology, Inc., Mount Kisco, NY.
Plastics Additives and Modifiers Handbook, Jesse Edenbaum, Ed. Van Nostrand Reinhold, New York, 1992, pp. 497-500.
Kaolins for the Paper Industry, Engelhard.
J. H. Foott et al., "Whitewash Found Harmless in Applications on Walnut Leaves," *California Agriculture* (Mar. 1967), pp. 2-3.
Federation of Societies for Coatings Technology (FCST), data sheets for "Calcium Carbonate" and "China Clay or Aluminum Silicate," 1981, pp. 10-13, 24-27.
Lori Thomson Harvey, A Guide to Agricultural Spray Adjuvants Used in the United States. Fresno, Thomson Publications (1988-89 Edition), pp. 7, 10, 17, 19, 31, 45, 50, 56.
Eugene Hecht, Optics. Second Edition. USA: Addison-Wesley Publishing Company (1987), p. 294.
W. T. Horne, "Climatic Injuries to Fruit Trees," *The University of California Journal of Agriculture*, vol. VI (1) (1920), pp. 25-26.
W. F. Hower, "Adsorption of Surfactants on Montmorillonite," *Clay and Clay Minerals*, vol. 18 (1970), pp. 97-105.
C. R. Hunt, "Toxicity of Insecticide Dust Diluents and Carriers to Larvae of the Mexican Bean Beetle," *Journal of Economic Entomology*, vol. 40 (1947), pp. 215-19.
Kaolin Clays and Their Industrial Uses, J. M. Huber Corporation, New York (1949), pp. 131-35.
Textbook for Lacquers and Coatings. Volume II. Pigments, Fillers, Paints. Hans Kittel, Ed., W. A. Colomb in der H. Heenemann GmbH, Berlin (1974), pp. 372-73.
Columbia River Carbonates, Microna S-90 H.B., Dec. 1995.
R. Lemeur, "Reflectant Induced Modification of Soybean Canopy Radiation Balance. II. Quantitative and Qualitative Analysis of Radiation Reflected from a Green Soybean Canopy," Agronomy Journal, vol. 67 (1975), pp. 301-306.
W. J. Lipton et al., "Whitewashing to Prevent Sunburn of 'Crenshaw' Melons," *HortScience*, vol. 6(4) (1971), pp. 343-45.
"Whitewash Boosts Walnut Production," Lodi News-Sentinel, Dec. 7, 1963, p. 6.
A. J. Loustalot, "Apparent Photosynthesis and Transpiration of Pecan Leaves Treated with Bordeaux Mixture and Lead Arsenate," *Journal of Agricultural Research*, vol. 68(1) (1944), pp. 11-19.
I. Mackinnon et al., "Kaolinite Particle Sizes in the <2 μm Range Using Laser Scattering," Clay and Clay Minerals, vol. 41(5) (1993), pp. 613-23.
S. Marco et al., Suppression of Powdery Mildew in Squash by Applications of Whitewash, Clay and Antitranspirant Materials, *Phytoparasitica*, vol. 22(1) (1994), pp. 19-29.
W. C. Micke et al., "Water base paints for sunburn protection of young fruit trees," *California Agriculture*, vol. 20(7) (1966), p. 7.
S. Moreshet et al., "Effect of Increasing Foliage Reflectance on the CO2 Uptake and Transpiration Resistance of a Grain Sorghum Crop," *Agronomy Journal*, vol. 69 (1977), pp. 246-50.
S. Moreshet et al., "Effect of Increasing Foliage Reflectance on Yield, Growth, and Physiological Behavior of a Dryland Cotton Crop," *Crop Science*, vol. 19 (1979), pp. 863-68.
A. M. Nonomura et al., "The path of carbon in photosynthesis: Improved crop yields with methanol," *Proc. Natl. Acad. Sci. USA*, vol. 89 (1992), pp. 9794-98.
S. N. Ogbuehi et al., "Reflectorized Soybean Canopy in Relation to Transpiration and Herbicide Phytotoxicity," *Bull. Environm. Contam. Toxicol.*, vol. 25 (1980), pp. 879-83.
B. B. Patil et al., "Studies on the effect of nitrogen fertilizer, row spacing and use of antitranspirants on rapeseed (*Brassica campestris*) grown under dryland conditions," *J. Agric. Sci., Comb.*, vol. 91 (1978), pp. 257-64.
F. J. Perry et al., "Whitewash trials in walnuts," *California Agriculture* (Jun. 1970), pp. 8-10.
G. T. Powell, "Intensive Farming," in Twenty-First Annual Report of the Ontario Agricultural and Experimental Union. 1899. Toronto, Warwick Bro's & Rutter, Printers (1900), pp. 42-50.
C. E. Renshaw et al., "Permeability reductions induced by sorption of surfactant," *Water Resources Research*, vol. 33(3) (1997), pp. 371-78.
R. H. Robinson, Sprays. Their Preparation and Use. Station Bulletin 393. Corvallis, Oregon State College (May 1941), pp. 5-34.
N. J. Rosenberg, "Chapter 8—Improving Land and Water Use Practices," in Water Scarcity: Impacts on Western Agriculture, E. A. Engelbert and A. F. Scheuring, Eds., Berkeley, University of California Press (1984).
James F. Rusling, "Surfactant-Intercalated Clay Films Containing Metal Phthalocyanines," *Langmuir*, vol. 8(10) (1992), pp. 2455-60.
I. Seginer, "The Effect of Albedo on the Evapotranspiration Rate," *Agricultural Meteorology*, vol. 6 (1969), pp. 5-31.
E. F. Serr et al., "Effects of Whitewash Cover Sprays on Persian Walnuts in California," *Proceedings of the American Society for Horticultural Science*, vol. 82 (1963), pp. 243-49.
G. S. Sibbett et al., "Effect of a topically applied whitener on sun damage to Granny Smith apples," *California Agriculture*, vol. 45(1) (1991), pp. 9-10.
F. W. Southwick et al., "Influence of Bordeaux Mixture and Its Component Parts on Transpiration and Apparent Photosynthesis of Apple Leaves," *Plant Physiology*, vol. 16(4) (1941), pp. 721-754.

(56) References Cited

OTHER PUBLICATIONS

G. Stanhill et al., "The Effect of Reflecting Surfaces on the Solar Radiation Regime and Carbon Dioxide Fixation of a Glasshouse Rose Crop," *J. Amer. Soc. Hort. Sci.*, vol. 100(2) (1975), pp. 112-15.
G. Stanhill et al., "Effect of Increasing Foliage and Soil Reflectivity on the Yield and Water Use Efficiency of Grain Sorghum," *Agronomy Journal*, vol. 68 (1976), pp. 329-32.
Kosaku Suga et al., "Structural Characterization of Surfactant and Clay-Surfactant Films of Micrometer Thickness by FT-IR Spectroscopy," *Langmuir*, vol. 9 (1993), pp. 3649-55.
C. Thieme et al., "Precipitated Calcium Carbonate," in Pigment Handbook. Volume 1. Properties and Economics. Second Edition, P. Lewis, Ed., New York, John Wiley & Sons (1988), pp. 97-109.
K. R. Vijayakumar et al., "Prevention of Photo-induced Chlorophyll Loss by the Use of Lime Reflectant on the Leaves of Black Pepper (*Piper nigrum L.*)," *Agricultural and Forest Meteorology*, vol. 34 (1985), pp. 17-20.
T. C. Vogelmann et al., Leaves and light capture: light propagation and gradients of carbon fixation within leaves, *Trends in Plant Science*, vol. 1(2) (1996), pp. 65-70.
W. E. Wallace et al., "Dipalmitoyl Lecithin Surfactant Adsorption by Kaolin Dust in Vitro," *Journal of Colloid and Interface Science*, vol. 51(3) (1975), pp. 535-37.
W. E. Wallace et al., "Contrasting Respirable Quartz and Kaolin Retention of Lecithin Surfactant and Expression of Membranolytic Activity Following Phospholipase A2 Digestion," *Journal of Toxicology and Environmental Health*, vol. 37(3) (1992), pp. 391-409.
M. N. Westwood, Temperate-Zone Pomology, San Francisco, W. H. Freeman and Company (1978), pp. 299-332.
J. C. Whitten, "Winter Protection of the Peach," in University of the State of Missouri. College of Agriculture and Mechanic Arts. Agricultural Experiment Station. Annual Report. 1896. Columbia, Burckhartt & Rice, Printers (1896), pp. 140-59.
J. M. Witt, "Surfactants. Agricultural Spray Adjuvants," in Pacific North West Plant Disease Control Handbook, Extension Services of Oregon State University, Washington State University, and the University of Idaho (Mar. 1985), pp. 152-53.
W. W. Yates, Thesis on a Study of the Effect of Accessory Substances on the Adherence of Lime Sulfur Spray to the Integuments of Insects, Master of Science Thesis, Oregon State Agricultural College (1932).
V. Cantore et al., "Kaolin-based particle film technology affects tomato physiology, yield and quality," *Environmental and Experimental Botany*(2009).
Carolyn DeBuse et al., "Kaolin Particle Clay Film Effects on Physiology, Quality, and Productivity in Tulare and Howard Walnut," Walnut Research Reports 2010, California Walnut Board, pp. 269-82.
D. Michael Glenn et al., "Particle Films Affect Carbon Assimilation and Yield in 'Empire' Apple," *J. Amer. Hort. Sci.*, vol. 128(3) (2003), pp. 356-62.
L. Panella et al., "Influence of Methanol on Sugarbeet Yield and Photosynthesis," *Journal of Sugar Beet Research*, vol. 37(2), pp. 55-72.
V. M. Russo et al., "Kaolin-based Particle Film Has No Effect on Physiological Measurements, Disease Incidence or Yield in Peppers," *HortScience*, vol. 40(1) (2005), pp. 98-101.
A. Theodoridou et al., "Light-dependent induction of strongly increased microalgal growth by methanol," *Biochimica et Biophysica Acta*, vol. 1573 (2002), pp. 189-198.
I. Zbiec et al., "Effect of Methanol on Some Plants," *Romanian Agricultural Research*, vol. 7-8 (1997), pp. 45-49.
Y. Zheng et al., "Effect of Methanol on Photosynthesis and Chlorophyll Fluorescence of Flag Leaves of Winter Wheat," *Agricultural Sciences in China*, vol. 7(4) (2008), pp. 432-37.
Leonardo Lombardini et al., "Effects of Particle Film Application on Leaf Gas Exchange, Water Relations, Nut Yield, and Insect Populations in Mature Pecan Trees," *HortScience*, vol. 40(5) (2005), pp. 1376-80.
D. Michael Glenn et al., "Particle Films: A New Technology for Agriculture," *Horticultural Reviews*, vol. 31 (2005), pp. 1-44.

Paul C. Doraiswamy et al., "Reflectant Induced Modification of Soybean Canopy Radiation Balance. I. Preliminary Tests with a Kaolinite Reflectant," *Agronomy Journal*, vol. 66 (1974), pp. 224-8.
B. B. Patil et al., "Influence of Antitranspirants on Rapeseed (Brassica campestris) Plants under Water-stressed and Nonstressed Conditions," *Plant Physiol.*, vol. 57 (1976), pp. 941-43.
"Heat and Walnuts," *Diamond Walnut News*, Feb., 1970, pp. 8-9.
David C. Davenport, "Reducing transpiration to conserve water in soil and plants," *California Agriculture*, May 1977, pp. 40-41.
Gary J. Puterka et al., "Kaolin-Based Particle Films for Arthropod Control," in Encyclopedia of Entomology, 2nd Ed., Springer Science+Business Media B.V., 2008, pp. 2075-80.
D. Michael Glenn et al., "Particle Film Application Influences Apple Leaf Physiology, Fruit Yield, and Fruit Quality," *J. Amer. Soc. Hort. Sci.*, vol. 126(2) (2001), pp. 175-81.
D. Michael Glenn et al., "A Reflective, Processed-Kaolin Particle Film Affects Fruit Temperature, Radiation Reflection, and Solar Injury in Apple," *J. Amer. Soc. Hort. Sci.*, vol. 127(2) (2002), pp. 188-93.
Gary Puterka et al., "Progress Toward Liquid Formulations of Particle Films for Insect and Disease Control in Pear," *Environmental Entomology*, vol. 29(2), pp. 329-39.
J. N. Wünsche et al., "'Surround' Particle Film Applications—Effects on Whole Canopy Physiology of Apple," Proc. XXVI International Horticultural Congress: Key Processes in the Growth and Cropping of Deciduous Fruit and Nut Trees, ISHS *Acta Hort.*, vol. 636 (2004), pp. 565-571.
M. le Grange et al., "Effect of Kaolin Applications on Apple Fruit Quality and Gas Exchange of Apple Leaves," Proc. XXVI International Horticultural Congress: Key Processes in the Growth and Cropping of Deciduous Fruit and Nut Trees, ISHS *Acta Hort.*, vol. 636 (2004), pp. 545-550.
M. S. Soundara et al., "Effect of Antitranspirants and Reflectants on Pod Yield of Rainfed Groundnut," *Agric. Sci. Digest*, vol. 1(4) (1981), pp. 205-6.
Surround® WP Crop Protectant label, Engelhard Corporation, 2004.
D. C. Davenport et al., "Antitranspirants . . . uses as effects on plant life," *California Agriculture*, May 1969, pp. 14-16.
M. Fuchs et al., "Effect of Increasing Foliage and Soil Reflectivity on the Solar Radiation Balance of Wide-row Grain Sorghum," *Agronomy Journal*, vol. 68 (1976), pp. 865-871.
E. T. Chittenden et al., "Calcium sprays for control of bitter pit and other disorders in apples," *N. Z. Journal of Experimental Agriculture*, vol. 1 (1973), pp. 85-91.
J. Basnizki et al., The Influence of a Reflectant on Leaf Temperature and Development of the Globe Artichoke (*Cynara scolymus L.*), *J. Amer. Hort. Sci.*, vol. 100(2) (1975), pp. 109-112.
A. H. Fitter et al., Environmental Physiology of Plants, Academic Press, New York, 1981, pp. 171-74.
D. C. Davenport et al., "Some Counteractive Effects of Antitranspirants," *Plant Physiol.*, vol. 49 (1972), pp. 722-24.
E. Fallahi et al., "The Role of Calcium and Nitrogen in Postharvest Quality and Disease Resistance of Apples," *HortScience*, vol. 32(5) (1997), pp. 831-35.
D. Sugar, "Enhanced Resistance to Side Rot in Pears Treated with Calcium Chloride During the Growing Season," *Plant Disease*, vol. 75(2) (1991), pp. 212-212-14.
J. Solárová et al., "Gas Exchange Regulation by Changing of Epidermal Conductance with Antitranspirants," *Photosynthetica* 15(3) (1981), pp. 365-400.
J. T. Woolley, "Relative Permeabilities of Plastic Films to Water and Carbon Dioxide," *Plant Physiol.*, vol. 42 (1967), pp. 641-43.
TIP 0106-05, Calcium carbonate pigment index, 1996.
TIS 0106-06, Kaolin clay pigment index, 1995.
J. Gale et al., "Plant Antitranspirants,"*Annu. Rev. Plant Physiol.*, vol. 17 (1966), pp. 269-81.
K. W. Brown et al., "Energy and $CO_2$ Balance of an Irrigated Sugar Bet (Beta vulgaris) Field in the Great Plains," *Agronomy Journal*, vol. 63 (1971), pp. 207-13.
J. D'A. Clark, Pulp Technology and Treatment for Paper, Second Ed., Miller Freeman Publications, Inc., San Francisco, 1985, pp. 774.
"Sun-Guard Beats Them All," Diamond Walnut News, Jun. 1971, pp. 13.

(56) References Cited

OTHER PUBLICATIONS

"Wilklay RP-80," SpecialChem S.A., 2012.
"Wilclay Wc Kaolin. White Airfloated Kaolin," 2008.
W. J. Lipton, Whitewashing Crenshaw and Cantaloup Melons to Reduce Solar Injury, Marketing Research Report No. 1045, Agricultural Research Service, U.S. Department of Agriculture, 1975.
N. K. S. Rao, "The effects of antitranspirants on leaf water status, stomatal resistance and yield in tomato," *Journal of Horticultural Science*, vol. 60(1) (1985), pp. 89-92.
N. K. S. Rao, "The effects of antitranspirants on stomatal opening, and the proline and relative water contents in the tomato," *Journal of Horticultural Science*, vol. 61(3) (1986), pp. 369-72.
S. K. Agarwal et al., "Effect of nitrogen rates, mulching and antitranspirants on water use and water use efficiency of barley (Hordeum vulgare L.) varieties grown under dryland conditions," *J. agric. Sci. Camb.*, vol. 92 (1979), pp. 263-68.
W. J. Lipton et al., "Solar Injury of 'Crenshaw' Muskmelons: The Influence of Ultraviolet Radiation and of High Tissue Temperatures," *Agricultural Meteorology*, vol. 22 (1980), pp. 235-47.
J. Gale, "Studies on Plant Antitranspirants," *Physiologia Plantarum*, vol. 14 (1961), pp. 777-86.
E. J. Hanson, "Sour Cherry Trees Respond to Foliar Boron Applications," *HortScience*, vol. 26(9) (1991), pp. 1142-45.
J. D. Spiers et al., "Effects of Kaolin Clay Application on Flower Bud Development, Fruit Quality and Yield, and Flower Thrips [Frankliniella spp. (Thysanoptera: Thripidae)] Populations of Blueberry Plants," Proceedings of the Ninth North American Blueberry Research and Extension Workers Conference, C. F. Forney et al., Eds., The Haworth Press, Inc., 2004, pp. 361-373.
J. R. Schupp et al., "Effect of Particle Film on Fruit Sunburn, Maturity and Quality of 'Fuji' and 'Honeycrisp' Apples," *HortTechnology*, vol. 12(1) (2002), pp. 87-90.
L. Lombardini, Principal Investigator, Study of whole-canopy and leaf gas exchange, water relations, chlorophyll fluorescence to understand the effects of cultural practices on growth and productive capacity of apple trees, Final Report, WTFRC Project #AH-01-87, 2003.
Sun-Guard brochure, undated.
SUN-GUARD Agricultural Weatherproofing, Directions for Application.
Sun-Guard Agricultural Weatherproofing, Material Safety Data Sheet, May 15, 1986.
Sun-Guard Part II, Material Safety Data Sheet, Mar. 1, 1991.
Lecithin Emulsifying. ADM Specialty Products, undated.
Agro-K Products, downloaded Nov. 9, 2011.
Welcome to Agro-K, downloaded Nov. 6, 2011.
Britz Haze. Sun Reflector. Specimen Label (2003).
Stoller Calcium 5X. Stoller Enterprises, Inc., undated.
Calcium Plus. Omnia Nutriology, 2010.
Cocoon. Crop Sunburn & Heat Stress Protectant. Advan LLC, undated.
Cocoon Material Safety Data Sheet. Advan LLC, Jun. 30, 2008.
Cocoon record from USPTO Trademark Electronic Search System.
Crop Solution. Crop Block. Liquid Sun Block. Ultimate Agri-Products, undated.
Green Cypress record from USPTO Trademark Electronic Search System.
Green Cypress Kaolin Crop Spray for Crop Sunburn Protection. Monterey AgResources, undated.
Green Cypress Kaolin Crop Spray Material Safety Data Sheet. Monterey AgResources, Jul. 2004.
KaMin™ 90 Water Washed Kaolin Clay. KaMin LLC, Jan. 1, 2009.
Kamin record from USPTO Trademark Electronic Search System.
Stoller Key Feeds DF Calcium. StollerUSA, undated.
Kool-Kore™ for Crop Sunburn Protection. Northwest Agricultural Products, 2002/2003.
Kool Kore™ Material Safety Data Sheet. Northwest Agricultural Products, Inc., undated.
Limestone-F. W A Cleary Chemical Corporation, Feb. 1980.
Limestone-F Specimen Label. W A Cleary Chemical Corporation, Jul. 1993.
Limestone F. Liquid Flowable Limestone. Cleary Chemical Corporation, Oct. 1997.
U.S.A. Lithovit®. All Natural Foliar Nutrient. Zeovita GmbH, undated.
Lithovit® Natural $CO_2$ Foliar Fertilizer. Zeovita GmbH, undated.
Lithovit record from USPTO Trademark Electronic Search System.
Magnum Fill® 70% Precipitated Calcium Carbonate. Mississippi Lime, Dec. 2007.
Magnum Fill record from USPTO Trademark Electronic Search System.
Magnum Gloss® 72% Precipitated Calcium Carbonate. Mississippi Lime, Oct. 2006.
Magnum Gloss record from USPTO Trademark Electronic Search System.
"Laser Diffraction Particle Size Measurement of Food and Dairy Emulsions Using Equipment From Malvern," dated Apr. 20, 2005, downloaded on Nov. 8, 2011 from http://www.azom.com/article.aspx?ArticleID=2808.
Monterey Crop-White for Crop Sunburn Protection. Monterey AgResources, undated.
"Agricultural spray adjuvant," downloaded on Sep. 23, 2011 from http://en.wikipedia.org/wiki/Agricultural_spray_adjuvant.
Monterey Crop-White for Crop Sunburn Protection label. Monterey Chemical Co., undated.
"Crop Fertilizers and Soil Amendments," OMRI Products List, Web Edition, Nov. 4, 2011.
OMYACARB record from USPTO Trademark Electronic Search System.
Omyacarb® F T 13 CG. Omya Columbia S.A, Oct. 27, 2008.
Omyacarb® F T—FL. Omya Inc., Apr. 21, 2010.
Omyacarb® UF—FL. Omya Inc., Apr. 2, 2010.
Omycarb® UF . OMYA, Inc., undated.
Omyacarb® UFT—FL. Omya Inc., Apr. 21, 2010.
PIT-STOP® Dry Concentrate Foliar Calcium 32.5%. Loveland Products, Inc., undated.
PIT STOP record from USPTO Trademark Electronic Search System.
Raynox® Apple Sunburn Protectant. Pace International, LLC, "040308.".
RAYNOX records from USPTO Trademark Electronic Search System.
Raynox® Apple Sunburn Protectant. Undated.
"Kaolin Clay" and "Diffusion," Wilbur-Ellis.
RED-TOP record from USPTO Trademark Electronic Search System.
SNOW record from USPTO Trademark Electronic Search System.
Red-top SNOW® specimen label. Wilbur-Ellis Company.
RED-TOP SNOW®. Wilbur-Ellis Company.
"Crop Microclimate Management and Certis USA Enter into Agreements to Develop New Plant Stress Technologies," Nov. 16, 2010.
"Screen" record from USPTO Trademark Electronic Search System.
Screen™ Duo. Crop Microclimate Management Inc.
Screen™ Duo. Fortified Heat Stress Protection for Plants. Crop Microclimate Management Inc.
S-K-H Organic Adhesive Adjuvant. Monterey AgResources, "0803/0905(02).".
S-K-H Organic Adhesive Adjuvant. Material Safety Data Sheet. Monterey AgResources, Sep. 2005.
SNOCAL 70. Technical Service Bulletin 601. Standard Industrial Minerals, Inc., "Received at Fresno Sep. 16, 1981.".
Sun-Guard. Sun-Guard Chemical Company.
SUN-GUARD Tests Conducted by University of California and Others. SUN-GUARD Chemical Company, Inc.
SUN-GUARD Agricultural Weatherproofing. Material Safety Data Sheet. Sun-Guard Chemical Company, Inc., Apr. 7, 2003.
SUN-GUARD PART II Agricultural Weatherproofing. Directions for Application. Sun-Guard Chemical Co., Inc.
SUN-GUARD PART II. Material Safety Data Sheet. Sun-Guard Chemical Company, Inc., Apr. 7, 2003.
1980 Whitewash Experiment—Processing Tomatoes. Yolo County—Madison.

(56) References Cited

OTHER PUBLICATIONS

1980 Whitewash Experiment—Processing Tomatoes. Yolo County—Esparto.
ORTHO records from USPTO Trademark Electronic Search System.
SUN-GUARD Agricultural Weatherproofing. Directions for Application. Sun-Guard Chemical Company, Inc.
Sun Shield. Ortho. Chevron Chemical Company. Undated.
ORTHO Sun Shield. Material Information Bulletin. Chevron, 1981.
SURROUND CF Crop Protectant, Material Safety Data Sheet. NovaSource, Tessenderlo Group, Jul. 9, 2009.
Performance Comparison, *Surround* v. *Liquid Sunscreen Products*. NovaSource, Tessenderlo Group, Jul. 2010.
TECH-FLO® CALCIUM. Product Bulletin No. 2. Nutrient Technologies, Inc., 1989.
TECH-FLO record from USPTO Trademark Electronic Search System.
Reflections™. Downloaded on Nov. 2, 2011 from http://www.tigercal.com/products/reflections.
TIGERCAL™ 30 Liquid Calcium. Tiger Industries Inc. Undated.
REFLECTIONS record from USPTO Trademark Electronic Search System.
TIGERCAL 30 record from USPTO Trademark Electronic Search System.

\* cited by examiner

Figure 3
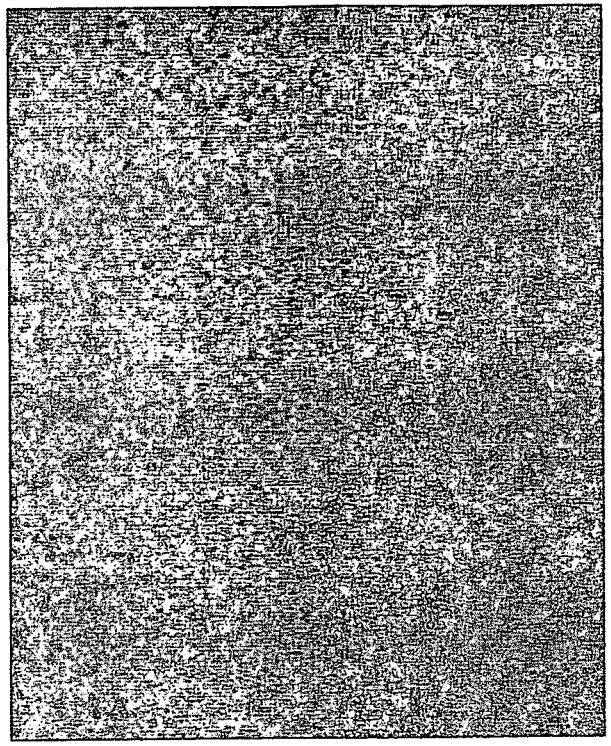
FIG. 3B
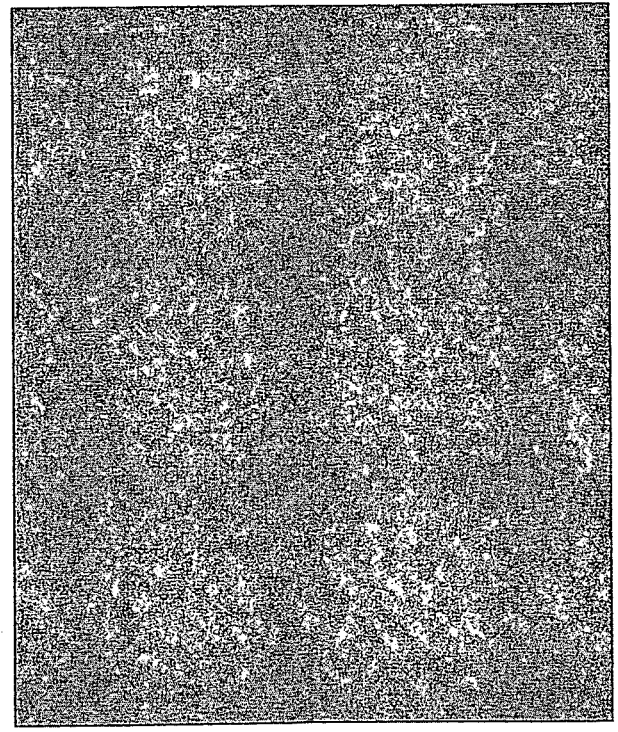
FIG. 3A

Figure 4
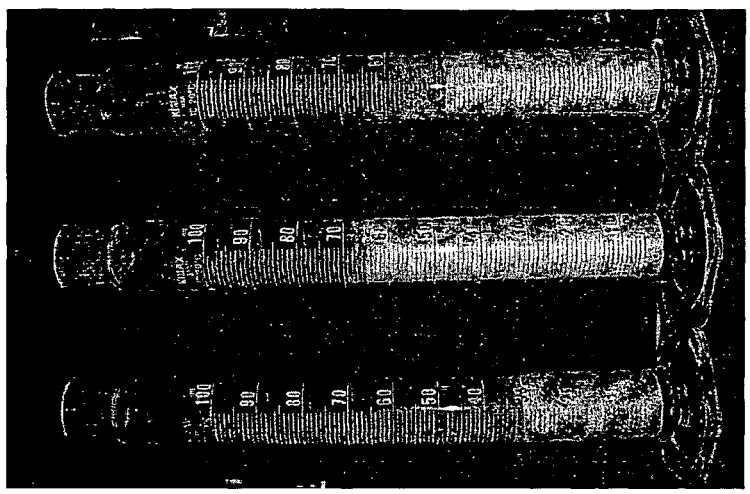
FIG. 4C
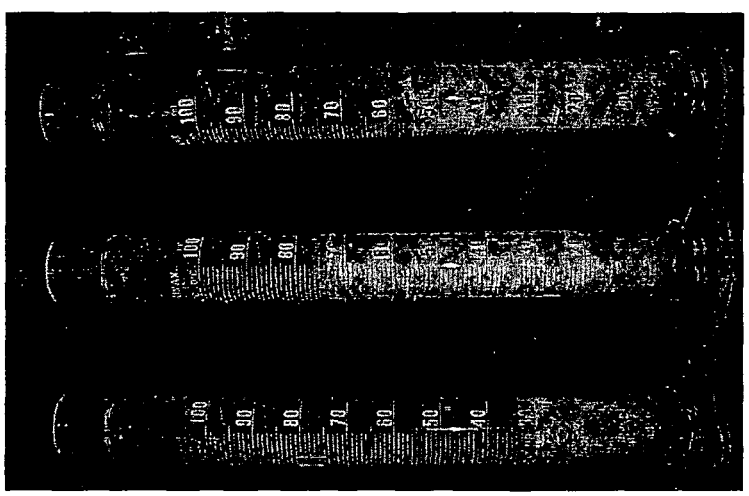
FIG. 4B
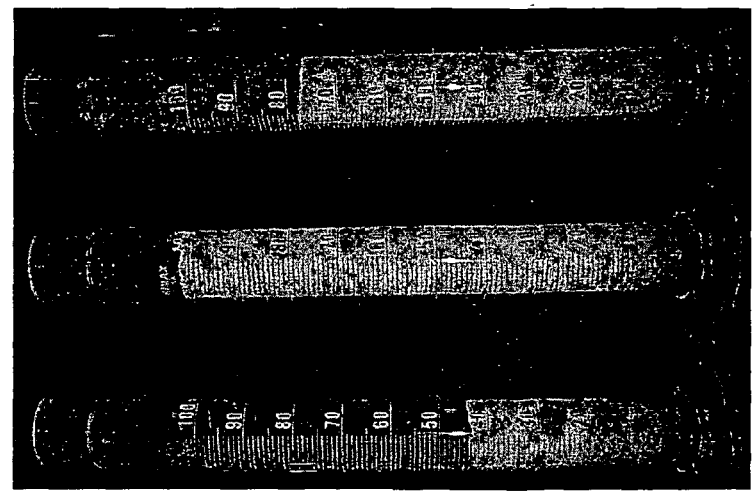
FIG. 4A

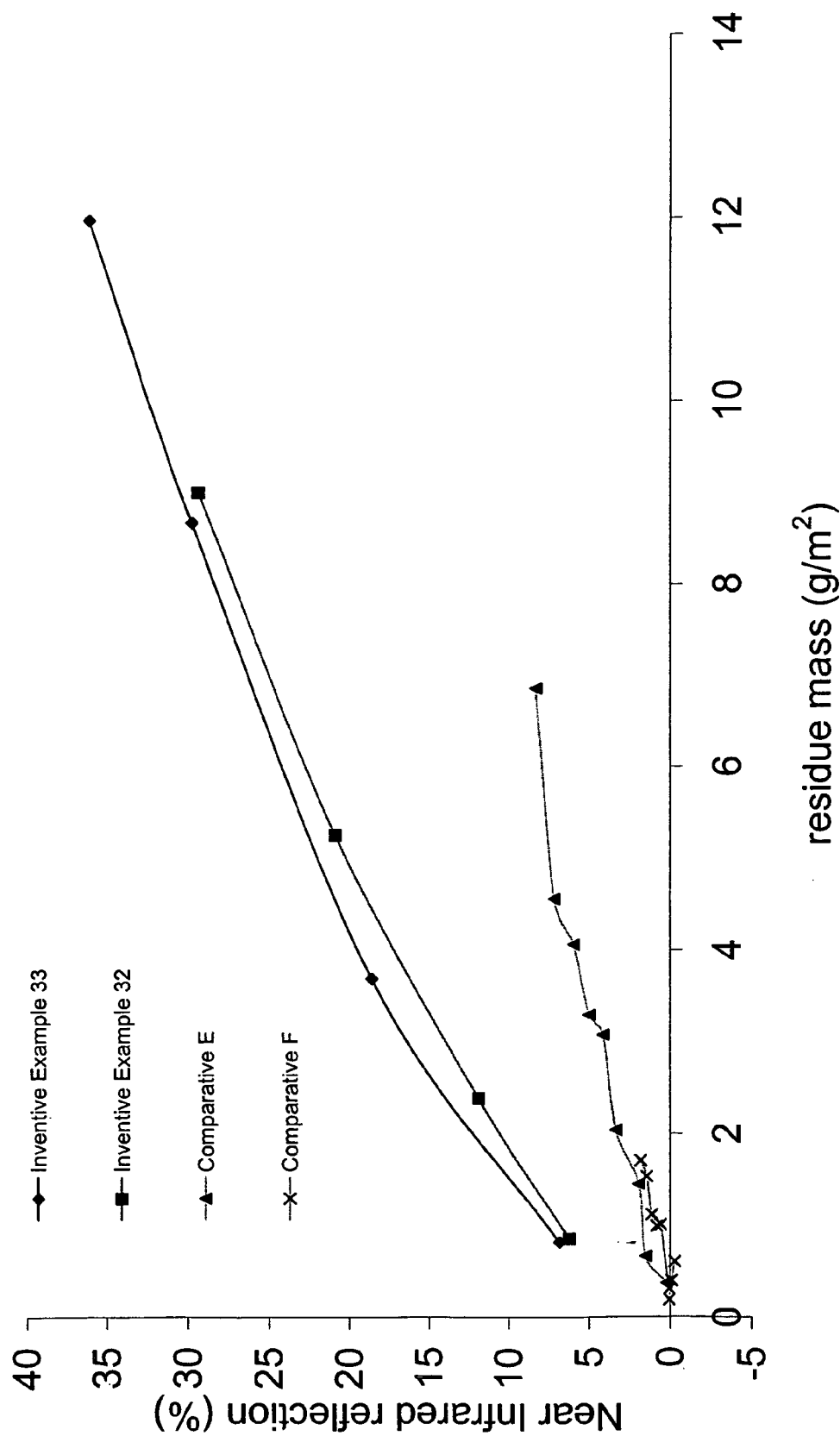

COMPOSITIONS COMPRISING PARTICLES RESULTING FROM PROCESSING IN A SLURRY MIX

This patent application claims priority to U.S. provisional patent application Ser. No. 60/594,745 filed May 3, 2005 and Ser. No. 60/594,918 filed May 18, 2005 incorporated herein by reference in their entireties.

BACKGROUND

Minerals, such as kaolin, in their crude or unprocessed state inherently contain a variety of impurities that are unique and specific to the deposit. In response to needs in agriculture, the present invention is directed to the water processing of highly impure to slightly impure minerals to make them useable, functional, improved in performance, and generally safer for agricultural particle film depositions. This processing is commonly referred to as either water processing or water washing in the mineral industry.

Kaolin clay, for example, generally uses two different processing methods to produce a "beneficiated", marketable material. These methods are commonly referred to as dry processing and wet processing. The dry process method generally produces a product that closely mirrors the properties originally found in the crude kaolin. Because of this, final products containing the desired particle size distribution, having low abrasivity, and having elevated brightness are typically determined by reliance on the quality of the deposit as determined by testing of the drilled core samples. With dry processing, the crude kaolin is simply crushed, dried, pulverized, and air floated to remove coarse grit particles.

A more recent development has been the wet processing method to produce higher quality products of more uniform and predetermined physical and chemical properties, which are less reliant on crude selection. Therefore, crude kaolins of widely varying ore quality may now be used to produce products which are more uniform and of higher marketable value. Because wet processing as a whole encompasses an extensive array of beneficiation processes, the final product can also vary with respect to the degree of quality, characteristics, and performance. Wet processing also allows for ease of manipulation of crude source and adjustment of final quality specification.

As disclosed at www.kaolin.co.za, or by testing, water-washed kaolin from Serina Kaolin in South Africa referred to as Serina Filler Grade may be used as a pesticide carrier. A finer particle size product called Serina Ultrafine is listed for paint, rubber, and ceramic applications but not for pesticide carrier use. In the following Table 1, the Serina properties are summarized.

TABLE 1

| Trade Name | Crystalline Silica (%) | Particle Size | Residue On 45 Micron Screen (%) | Einlehner Abrasion | Elrepho Brightness | pH | Mean particle size, psd (microns) |
|---|---|---|---|---|---|---|---|
| Serina Filler Grade - U | 0.58 | 48% less than 2 microns | 0.20 | 35 | 83% | 5 | 2.1 |
| Serina Filler Grade - N | 3.04 | 48% less than 2 microns | 0.20 | 35 | 83% | 5 | 2.62 |
| Serina Ultrafine | Not listed or tested | 70% less than 2 microns | 0 | Not listed or tested | 83% | 4-5 | Not listed or tested |

The processing noted for the Serina products indicates a minimum level of water processing (beneficiation) as indicated by the properties shown. The particle size has not been made finer than 70%<2 microns. This is considered to be coarse by water processing standards as marketed for decades, for example, by kaolin producers in Georgia, USA, Brazil, and the United Kingdom for many uses. The 45 micron screen residue for the Filler Grade is 0.2 and Ultrafine grade is noted as 0% which by implication of the significant figures indicates a range of 0.49% and lower. The brightness of both has not been raised above 83% indicating little or no brightness beneficiation. The Einlehner Abrasion of 35 for the Serina Filler grade is high versus water-processed kaolin used in paper and paints which generally is less than 10. The pH's of 5 or 4.0 to 5.0 is in the range of typical natural pH of kaolin in the ground and indicates that no pH adjustment was made and no alkaline (basic) or otherwise neutralizing additives are present. Neither tested grade, U or N (Comparative A below), has a crystalline silica content below 0.20%.

The website describes under "Refining Process" the following: Serina Filler grade: Wet milling, screening and hydrocyclone beneficiation followed by mechanical-thermal drying and Serina Ultrafine grade: Water washing, hydrocyclone beneficiation and screening followed by mechanical-thermal drying. These descriptions confirm a minimum level of water processing such as the use of hydrocyclones and screens and no utilization of commonly known state of the art processes. The products are both offered as powder and pellet form. No product in spray dried bead form is noted.

U.S. Pat. No. 4,738,726 teaches that a dispersant is used at 0.025 to 0.2% by weight based on the weight of the dry clay. The clay is used for coating paper.

U.S. Pat. No. 6,110,867 discloses the use of hydrous kaolin for application to horticultural crops for enhancing photosynthesis but no mention is made of the properties of the hydrous kaolin or the presence of a chemical additive. Kaolins that are substantially free of crystalline silica and low in titanium have been used as inert fillers, diluents, or adjuvants in low concentrations in wettable powder and dry flowable type agricultural sprays. Levels of kaolins used in these applications are sub-functional for effective use as agricultural particle films and, in addition, are not formulated to be effective particle films. For tree crops, for example, kaolin wettable powder and dry flowable chemical pesticide sprays are used at about 0.5-6 lbs per acre on medium sized trees. Vines and bushes usually require about half of these amounts and low-growing row crops about a fourth to half of these amounts. Maximum use of a kaolin wettable powder or dry flowable for very large trees using 200 gallons per acre of water would be about 12 lbs per acre. Kaolin typically makes up 80 to 95% of the composition but may be less as cited by commonly assigned U.S. Pat. No. 7,018,643B2 on Pesticide Delivery System. Kaolin wettable powder and dry flowable chemical pesticide sprays contain additives such as pesticides.

In comparison, agricultural particle films use much higher levels of mineral particles per given area of substrate. For example, a composition (95% kaolin and 5% "other") called SURROUND® WP crop protectant is used as an agricultural particle film. Surround WP crop protectant instructs on its labels to use concentrations of 20.8 to 50 lbs per 100 gallons or 2.5 to 6% wt/wt in sprays. Per the directions for use, medium sized trees use 20.8 to 50 lbs per acre per spray. Vines and bushes usually require about half of these amounts, and low-growing row crops about a fourth to half of this amount. Use of Surround WP crop protectant for very large trees using 200 gallons per acre of water would be 50 to 100 lbs per acre.

Kaolin deposition difference between particle films and kaolin wettable powders or dry flowable type compositions can be considered by average theoretical application mass of mineral per given area of substrate. For example, for an orchard of 200 trees/acre, with the average leaf area of a single tree of 35m$^2$, there would be about 14,000 m$^2$ of leaf area for the entire orchard, including the top and bottom leaf surface. A 20.8 lb (19.76 lbs of kaolin mineral at 95%) application of Surround WP particle film, which is the minimum use level, calculates to an average theoretical kaolin deposition of about 63 ug/cm$^2$. In comparison, the maximum average deposition level of mineral in a kaolin wettable powder or dry flowable type would have a deposition of about 15 to 18 ug/cm$^2$. FIG. 1 shows SURROUND® WP crop protectant has undissolved particles; this means that chemical additive is not uniformly distributed among or on the main kaolin (as defined below).

Per the labeled application rate, a commercially available wax and bentonite agricultural product called Raynox delivers about 1 lb of bentonite mineral component per acre. (The labeled rate of Raynox is up to 2.5 gallons per acre. If the density of Raynox is 8 lbs per gallon at 5% mineral, this equals only 1 lb of bentonite per acre.) It is not known if the bentonite mineral component is wet processed. U.S. Patent Application Publication 2004/0146617 discloses the use of bentonite for application to fruits and vegetables.

Typical deficiencies associated with the non-water washing manufacturing process are a non-uniform and relatively coarse particle size distribution, moderate to poor optical properties in coatings, low brightness, and the presence of impurities such as crystalline silica, base metal oxides such as titanium oxides, naturally occurring salts, and trace heavy metals. Some impurities may be present in such a high concentration as to make the product unsafe and virtually unusable, one example being kaolin deposits found in Spain and other locations, which can contain up to 1/3 crystalline silica and are referred to as kaolinitic sand. Another example is Georgia, USA kaolin, which is relatively higher in purity, but may contain elevated levels of base metal oxides such as titanium dioxide.

It can generally be stated that the presence of crystalline silica impurities is considered highly undesirable due to the inherent abrasiveness of the material and for health and safety concerns which crystalline silica imposes. Coarse crystalline silica particle fractions are extremely hard and abrasive materials. When present at elevated levels and applied in high concentrations, such as in particle film applications, crystalline silica will cause unnecessary equipment wear and premature equipment failure. The added scouring effect which crystalline silica can cause on contact surfaces will also result in the unwanted delivery of dislodged contaminates such as toxic metals and the like. In addition, when formulated and delivered as an agricultural spray, the abrasive particle contaminates can produce wounding of the horticultural surface which may further result in decreased disease tolerance, decreased pest resistance and increased phytotoxicity. Fine crystalline silica particle fractions are undesirable because they are a pulmonary carcinogen and inhalation hazard and are typically not adequately removed through non-water washed, processing methods. IARC has classified crystalline silica as a carcinogen.

Typically, the sedimentary kaolin deposits found in the United States (Georgia and South Carolina), are considered to be of a higher crude quality as they contain lower levels of crystalline silica, are of a finer particle size distribution, are generally brighter, are relatively abundant and are found close to the surface allowing for ease of mining and recovery. One negative aspect of these kaolins is that they contain higher levels of titanium-based impurities. Titanium oxides can negatively affect color. Therefore, a less intense method of processing is necessary to remove the crystalline silica fraction which may be present, but special water processing steps are required to lower the levels of the base metal oxide. In addition, the removal of the titanium oxide impurities will generally increase the optical brightness of the finished material and produce a product containing a higher concentration of kaolin mineral.

Non-water-washed products are manufactured by drying, crushing, and milling crude minerals. In some, through air "floating" the useful fine particle segment is captured and the coarse product is discarded. Air floating has the ability to remove particles that are either greater in mass than the desired mineral or are not attached to the desired mineral. The resulting non-water washed product has a crystalline silica content from about 3 to about 36 weight percent. In the following Table 2, the properties of commercially available agricultural compositions comprising air processed kaolin are summarized and PSD stands for (average) particle size distribution.

TABLE 2

| Trade Name | Crystalline Silica (%) | +325 Residue (%) | Einlehner (mg/100k rev) | TiO$_2$ (%) | GE Brightness | PSD (microns) |
|---|---|---|---|---|---|---|
| CropWhite | 25.40 | 5.50 | 172 | 0.33 | 77.7 | 3.2 |
| Snow | 25.3 | 3.6 | 188 | 0.32 | 75.5 | 6.3 |
| Sunguard | 5.00 | 1.61 | 30 | 2.00 | 70.2 | 1.4 |
| Sombreador | 2.91 | 0.49 | 232 | 0.41 | 73.9 | 3.6 |
| M.A.F.A. Leroia | 36.19 | 9.30 | 238 | 0.41 | 74 | NA |
| A.B.S.A. 45 | 4.42 | 8.60 | 238 | 0.30 | 74.4 | 4.1 |

It is common in many industries to use a chemical such as a surfactant to aid slurry handling and deposition properties. The chemical additive is dispersed in the slurry. In agriculture, a slurry of unrefined or air-floated minerals such as kaolin or calcium carbonate, or other minerals, have been commonly made by growers in spray tanks, often with a chemical dispersant added prior to application to a substrate. These compositions do not have the chemical additive "uniformly distributed among or on the functional particles" (as defined later).

SunBrite is a commercially available agricultural composition comprising a blend of limestone and titanium dioxide.

A commercial agricultural product called Raynox comprises primarily wax but it also has been found to contain hydrous kaolin that is not extensively processed and contains a high level of the surfactant and/or solvent morpholine.

A Material Safety Data Sheet from Columbia River Carbonates for Microna Shade calcium carbonate discloses that the limestone contains crystalline silica, typical levels are below 0.3 (w/w) in the product. No mention is made of the presence of a chemical additive.

One attractive agricultural particle film is provided by SURROUND® crop protectant available from Engelhard Corporation.

SUMMARY

Another attractive agricultural particle film is provided by the present composition. The present invention advantageously provides compositions resulting from processing in a slurry mix. The result of this liquid processing is functional particle compositions that are substantially free of crystalline silica and/or contain a chemical additive that is uniformly distributed among or on the particles.

Thus, the present invention provides an agricultural composition that comprises a functional mineral (defined below) that is substantially free of crystalline silica (defined below).

The term "mineral" as used herein includes finely divided (defined below) rocks such as granite, shale and the like that can contain silica in crude form but excludes hydrous kaolin, calcined kaolin, and bentonite. The phrase "functional mineral" as used herein means that the mineral forms a functional film deposition of particles known as an agricultural particle film.

The phrase "substantially free of crystalline silica" as used herein means crystalline silica content below 0.2 percent as determined using the NIOSH Manual of Analytical Methods, Fourth Edition, Crystalline Silica by xrd; Method 7500, Issue 3 (Jan. 15, 1998). This crystalline silica content is achieved by processing the starting material in a slurry mix. The term "slurry" as used herein means a suspension or mixture of insoluble starting material in a liquid medium or vehicle.

Also, the present invention provides a substrate having an agricultural composition thereon. The agricultural composition comprises a functional particle that is substantially free of crystalline silica selected from the group consisting of hydrous kaolin (defined below) or bentonite (defined below) and the composition is present at greater than or equal to about an average of 20 micrograms per square centimeter on the substrate.

The phrase "hydrous kaolin" as used herein means finely divided (defined below) kaolin that comprises substantially the original hydrous kaolin crystal structure with crystalline bound hydroxyl groups known as the water of hydration. "Hydrous kaolin" as used herein may be heat treated up to 400° C. as long as the original hydrous kaolin crystal structure with crystalline bound hydroxyl groups are substantially present or, at least, partially present. The phrase "functional hydrous kaolin" as used herein means that the finely divided (as defined below) hydrous kaolin forms a functional film deposition of particles known as an agricultural particle film. This use is in contrast to hydrous kaolin inert fillers, diluents, and adjuvants discussed above that are not applied in concentrations high enough nor are formulated to form a functional film of particles.

The term "bentonite" as used herein means finely divided (defined below) bentonite that is not heat treated at 175° C. or greater. The phrase "functional bentonite" as used herein means that the bentonite forms a functional film deposition of particles known as an agricultural particle film. This use is in contrast to bentonite inert fillers, diluents, and adjuvants discussed above that are not applied in concentrations high enough nor are formulated to form a functional film of particles.

The phrase "uniformly distributed among or on the functional" particles as used herein means that the chemical additive or active ingredient is substantially homogeneously distributed throughout the composition of dry particles or particles in a slurry or paste form that are concentrated well above the normal spray use level prior to application to the substrate; and was accomplished in a slurry mix. Excluded from this definition are slurries, for example, made in agricultural spray mix tanks with a chemical that is dispersed throughout the composition, and applied to a substrate without being converted into a dry, paste or concentrated slurry form even if the slurry was concentrated at 2 to 4 times during the mixing process. For example, soluble chemical additives will be dissolved and thus, be more evenly distributed among or on the particles. Similarly, colloidal or non-colloidal chemical additives are dispersed in the slurry and are, or can be, in a smaller particle size than before being added to the slurry mix. The divided colloidal additives are evenly distributed among or on the particles. Analogously, insoluble chemical additives are evenly distributed among or on the particles. A spray-dried bead is one final product form that is only achieved through spray drying of slurry mix and generally has a diameter of about 10 to about 150 microns; these beads can be further heat treated to dehydroxylate the kaolin and thereby form what are referred to as microspheres. The ingredients in Surround® WP in the dry form before use would not be considered to be uniformly distributed as defined herein. Uniformly distributed as defined above may occur at the micro scale, macro scale, or both. In the macro scale for example, uniformity may not be observed at the microscopic level. However, any relatively large aliquot derived from a batch that has uniform distribution on the macro scale may have the chemical additive evenly distributed in such a way that any large aliquot has the same amount of chemical additive. However, in small aliquots, the chemical additive may not be observed to be evenly distributed. For example, in a batch of 100 cubic meters, any given aliquot of one cubic meter may have the same amount of chemical additive. However, in the same batch, aliquots of one cubic centimeter may not have the same amount of chemical additive.

The term "slurry" as used herein means a suspension or mixture of insoluble particles in a liquid medium or vehicle.

Also, the present invention provides a substrate having an agricultural composition thereon. The agricultural composition comprises functional kaolin particles that are substantially free of crystalline silica and the composition is present at greater than or equal to about an average of 20 micrograms per square centimeter on the substrate. A chemical additive is uniformly distributed among or on the functional kaolin particles.

Also, the present invention provides an agricultural composition comprising (a) a functional particle selected from the group consisting of mineral, natural calcium carbonate (defined below), synthetic substance (defined below), or non-minerals and (b) a chemical additive that is uniformly distributed among or on the functional particles.

The phrase "natural calcium carbonate" as used herein means finely divided (defined below) ground carbonitic rock such as limestone, dolomite, or marble including both wet-ground and dry-ground in either slurry or dry form. The phrase "functional natural calcium carbonate" as used herein means that the natural calcium carbonate forms a functional film deposition of particles known as an agricultural particle film.

The phrase "synthetic substance" as used herein means finely divided (defined below), man-made, and generally is substantially free of crystalline silica. The phrase "functional synthetic substance" as used herein means that the synthetic substance forms a functional film deposition of particles known as an agricultural film.

The present invention provides an end use composition (defined below) comprising or consisting essentially of: (a) a functional particle that is substantially free of silica selected from the group consisting of hydrous kaolin, bentonite, mineral, and natural calcium carbonate; and (b) a chemical additive that is uniformly distributed within or on the functional particle.

The phrase "end use composition" as used herein means a composition and/or product that is used as-is by the final consumer without being added to another substance(s), being mixed or blended with another substance(s), or being applied to another substance(s), or otherwise being further processed before being used. The phrase "end use composition" does not exclude compositions and/or products that are mixed with a liquid vehicle such as water or oil by the final consumer. End use compositions are commonly referred to as consumer products. The "consumer" as defined here is not limited to single persons and includes business consumers.

The present invention provides a method of making an agricultural composition comprising the steps of: (a) combining functional particles selected from the group consisting of hydrous kaolin, bentonite, mineral, non-mineral, or calcium carbonate with a chemical additive in slurry mix to uniformly distribute said chemical additive among or on the functional particles; and (b) removing the liquid from the slurry combination.

In response to the needs of the agricultural industry for agricultural particle films such as the previously mentioned Surround® crop protectant from Engelhard Corporation, which is used, for example, as a crop protectant, the present invention provides the use of water-processed and thereby refined industrial functional hydrous kaolin, functional bentonite, functional minerals, and functional natural calcium carbonate as improved particle film products. Advantageously, the present invention yields a concentrated form of functional hydrous kaolin, functional bentonite, and functional mineral that are substantially free of crystalline silica.

Agricultural particle films usually require a fine particle sized distribution product of high purity with a high number of finely divided individual particles per given weight. Increasing the sheer number of particles dramatically increases the product performance. This may be accomplished through the water processes of dispersion, screening, centrifugation, filtration, delamination, and/or a variety of other processes. Purification via water processing removes crystalline silica to levels that are generally undetectable by standard test. Levels of coarse contaminants that hamper practical use are also removed. In addition, an increase in final product brightness may be achieved through further processes such as bleaching, ultraflotation, trepping, ozonation, and magnetic separation.

Products made of water washed ingredients are more efficient in their performance and thus, require a lower material concentration to be applied compared with known products made by non-water washed methods. Products can also be created in improved product physical forms such as spray-dried beads which offer convenience and performance improvements. Water processing also offers the advantages of intimate blending of particles to create improved products and the capability of adding other functional chemicals that become homogenous in the product.

Thus, the present invention provides an agricultural composition comprising of at least one functional hydrous kaolin, functional bentonite, or functional mineral that is substantially free of crystalline silica and may alternately contain residual chemicals that enhance performance. The composition is then applied through dusting, spraying, foaming, painting or the like, preferably in a liquid vehicle carrier, or otherwise applied to leave a functional deposition, which is substantially greater than 90% mineral or less as disclosed in commonly assigned U.S. Pat. No. 7,018,643B2 on Pesticide Delivery System. This application of the present composition generates a particle film.

BRIEF DESCRIPTION OF THE DRAWINGS

FIG. 3 shows a film formed from an example of the present agricultural composition having a chemical additive that is uniformly distributed among or on the kaolin compared with a film formed from an agricultural composition that does not have an additive that is uniformly distributed among or on the kaolin.

FIG. 4 shows an example of the present agricultural composition comprising water processed hydrous kaolin both in unbeaded and beaded form compared with an air floated hydrous kaolin.

FIG. 6 shows other examples of the present agricultural compositions compared with commercial products.

DETAILED DESCRIPTION

Figure 1:
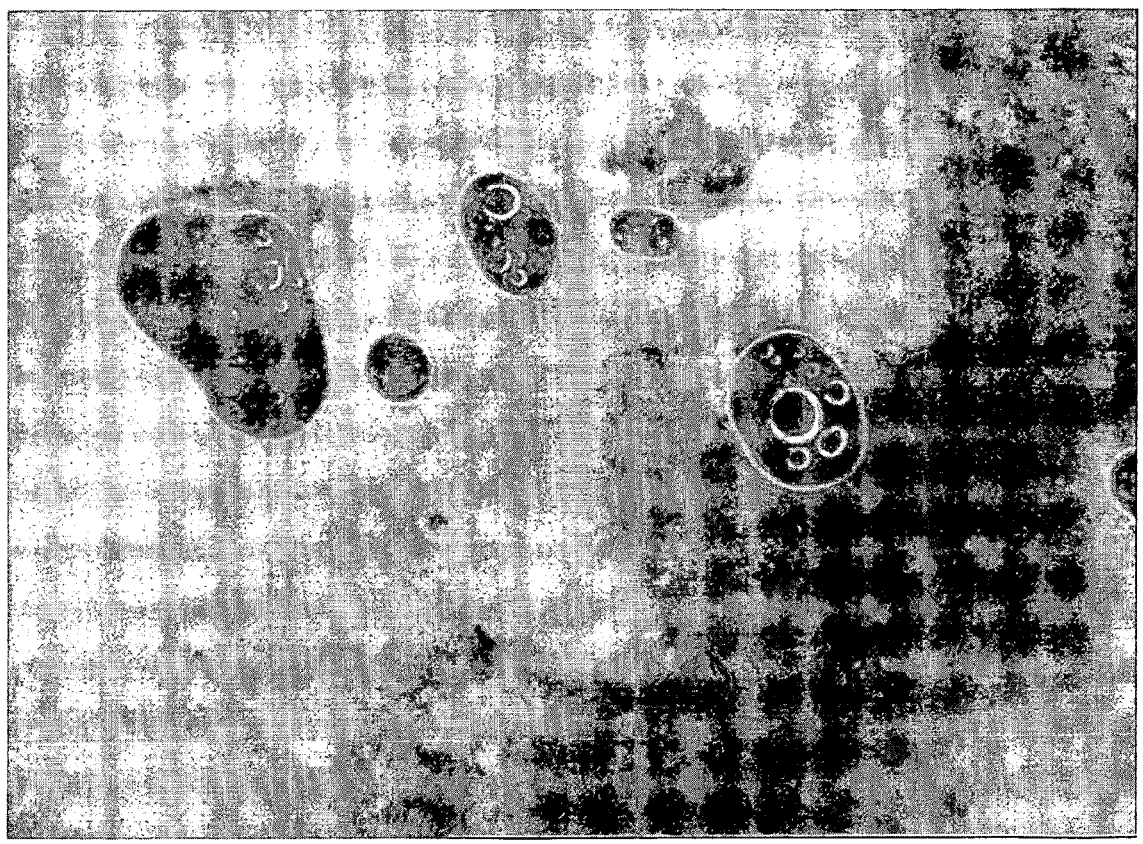
FIG. 1 shows SURROUND® WP crop protectant.

The phrase "active ingredient" as used herein means a chemical substance that has a biological effect. Examples of useful agricultural active ingredients include the functional substance in pesticides, plant growth regulators, sterilants, fertilizers, and biocides.

The term "TREP" as used herein means Titanium Removal and Extraction Process as practiced by certain kaolin producers.

The term "densified" as used herein means the process in which dried particles are re-wet and then dried in order to increase the mass per unit volume of the final product. The foregoing process is commonly referred to as prilling or agglomerating for the purpose of producing a better dry flowing product. The term "densified" also includes a characteristic of the product resulting from spray drying which inherently increases density.

Examples of preferred minerals include anhydrite; sillimanite group minerals such as andalusites, kyanites, sillimanites; staurolite, tripoli; tremolite; natural gypsum; anhydrite; asbestos materials; adobe materials; barites; bauxite; pumices, volcanic cinders, slags, scorias, expanded shales, volcanic cinders, carbonates such as limestones and dolomites; diamond dusts both synthetic and natural; emerys; micas such as biotites and muscovites; garnets; gilsonites; glauconites; vermiculites, fly ashes, ash waste, grogs (broken or crushed brick), shells (oyster, coquina, etc.); wash plant or mill tailings, phosphate rocks; potash; nepheline syenites, beryllium materials such as beryls; borons and borates, talcs, clay minerals such as fullers earths, ball clays, halloysites, refractory clays, flint clays, shales, fire clays, ceramic clays, coal containing kaolins, smectites (montmorillonite, saponites, hectorites, etc); hormites (attapulgites, pyropholites, sepiolites, etc.); olivines; feldspars; chalks; diatomaceous earths; insulation materials such as calcium silicates, glass fibers, mineral wools or rock wools; wollastonites; graphites; refractory materials; vermiculites; perlites; rare earth minerals; elemental sulfurs and other sulfur minerals; other insoluble elemental and salt compounds; other miscellaneous insoluble particles; other functional fillers such as, pyrogenic silicas, titanium minerals such as titanium dioxides, magnesium oxides, coal dust, magnesite, natural zeolite, and microspheres (spherical agglomerations of calcined kaolin particles generally larger than 10 microns in diameter), aluminum trihydrate, hollow mineral-based spheres, chemical or physically activated forms of any of the preceding, and acid-activated bentonite.

Useful non-minerals include hemps, cellulose pulp, and wood pulp.

Useful synthetic substances include precipitated calcium carbonates, micronized plastics, essentially non-crystalline silicas such as precipitated silica and fumed silica, hollow mineral-based and plastic spheres, synthetic aluminum trihydrate, synthetic zeolite, laponite, aluminum trihydrate, synthetic mica, and synthetic gypsum.

Useful kaolin types are commercially available from Engelhard Corporation. The phrase "crude kaolin" comprises 10-99 weight percent kaolin, sand, mica, dolomite, iron, titanium dioxide and other clays such as bentonite and sepiolite. These contaminants can either be loosely distributed in the crude or are attached to the kaolin particle.

The functional hydrous kaolin, functional bentonite, functional mineral, or functional calcium carbonate suitable for use in the present invention is finely divided. The term "finely divided" when utilized herein means that the functional hydrous kaolin, functional bentonite, functional mineral, or functional calcium carbonate has a median individual particle size (average diameter) below about 100 microns. Preferably, the functional hydrous kaolin, functional bentonite, functional mineral, or functional calcium carbonate has a median individual particle size of equal to or less than about 10 microns or less. Other embodiments follow:

| Median Particle Size |
| --- |
| Equal to or less than about three microns |
| Equal to or less than about one micron |
| Equal to or less than about 0.6 micron |
| Equal to or less than about 0.4 micron |
| Equal to or less than about 0.3 micron |

Preferably, the GE brightness of the functional hydrous kaolin, functional bentonite, functional mineral, and functional calcium carbonate is greater than or equal to 85. Preferably, the functional hydrous kaolin, functional bentonite, functional mineral, or functional calcium carbonate has an average particle size finer than 70% <2 microns. Average is defined as the point where 50% of the mass of particles is finer and 50% of the mass of particles is coarser.

Preferred water-processed minerals for making the present agricultural composition include, but are not limited to, HT®, LUSTRA®, ULTRACOTE™ ULTRA-WHITE®, ULTRA-GLOSS™, ASP® 170, ASP101, Gordon 70, ASP 400, ASP 900, and NUCLAY® kaolin, available from Engelhard Corporation.

Any combination of known water processing steps that are used to manufacture the preceding water-washed minerals may be used. Examples of such known water processing steps follow.

Crude kaolin, bentonite, or functional mineral is selected that has characteristics that allow the manufacture of particular products. The crude kaolin, bentonite, or mineral is examined for such attributes as color, lack of impurities, ability to be refined, viscosity effects in slurry, particle size, mineral content, consistency of the deposit, particle shape, and chemical or crystalline composition. Mineral crudes may also be blended to attain improved properties for a product. Crude blending may occur prior to beneficiation or, more optimally during water processing.

Air-floated kaolin, bentonite, or functional mineral may also be used as the starting material and may be processed by most or all of the following steps.

Kaolin, bentonite, or mineral may be pugged (kneaded) or extruded. Usually, the crude is pre-wet to a specific viscosity or consistency. These processes apply significant energy to the mineral and serve to mix and separate particles. These processes can be used to mix in other minerals or non-mineral additives.

Kaolin, bentonite, or mineral is made into an aqueous slurry and are blunged or otherwise beaten to separate it into individual particles. Processing chemicals are usually used to assist the separation into individual particles and to reduce viscosity such that processing solids can advantageously be raised. Selections of dispersed slurries from different crudes, or different raw crudes, or different mineral types, or different types of the same mineral can be blended to attain the best properties for a given product.

Degritting involves the removal of often non-targeted large particle size relatively hard mineral species including sand, crystalline silica, mica, and calcium carbonate from the crude. As a result, the degritted material has lower abrasion. Degritting may be partially done by air floating, or much more completely and thus preferably, by slurry passage through screens, centrifuges, hydrocyclones, or settling of gritty particles from the slurry.

Desliming involves settling of the desired fraction to leave the very fine particles of a colloidal nature in the supernatant liquor. The supernatant is pumped off and discarded or may be further processed and used as an industrial mineral itself.

Filtration commonly involves a cloth, paper, or screen filter such as a cloth drum filter with a vacuum to remove water, soluble contaminants such as salts, and excess processing chemicals. Alternatively, a filter press or Buchner filter may be used. The water washing process also has the added ability to remove water soluble reactive contaminates. These materials can be inherently phytotoxic in themselves and may react negatively when present in tank mixes with other chemical additives.

Dispersants are usually added to the centrifuge feed slurry material prior to the centrifuge in order to lower viscosity and help to separate particles. Centrifugation creates new particle size distributions through fractionation that are coarser or finer than the stream that was fed into the centrifuge. In the centrifuge, coarse particles are separated from fine particles in a controlled manner and both are separately captured.

Centrifugation is also a useful method for reducing the amount of impurities present in mineral. One useful centrifugation method is disclosed in U.S. Pat. No. 5,311,997 incorporated in its entirety herein by reference.

Particles are settled for fixed periods of time and particles that settle are separated both from excess water and fine particles that do not settle as rapidly as the others.

In delamination, relatively coarse plate-shaped particles such as kaolin are passed in slurry form through a delamination system comprised of various types of beads or other delamination media. The beads impact the kaolin "booklet," shear the booklet, and thus fracture the kaolin booklet particle into platelets. This results in a greater number of particles per given mass. These particles have a higher aspect ratio than the particles fed to the delaminator. The same may be accomplished by chemical intercalation whereby chemical separation of the individual platelets produces a more efficient lamina. An added benefit of delamination and chemical intercalation is that free impurities such as iron and titanium trapped within the kaolin lamina are able to be removed.

Bleaching may be accomplished through both oxidative and reduction means. The reductive method is preferred as it renders soluble therefore removable via washing and filtering certain trace compounds, such as iron that stains the particles and reactive compounds such as free iron.

In the case of kaolin, the pH of the kaolin slurry is lowered to an acid pH where reduction bleaches typically work best. Sodium hydrosulfite or other reducing chemicals are introduced. The slurry is pumped to a filter where the excess bleach and other soluble chemicals are pulled out by vacuum action.

Flotation is a useful method for reducing the amount of trace impurities such as titanium present in minerals like kaolin. One useful flotation method is disclosed in commonly assigned U.S. Pat. No. 6,378,703.

Dispersed kaolin pulp is transferred to a conditioning vessel prior to passage through a flotation cell. Typically the conditioning vessel is a high intensity mill capable of increasing the pulp temperature. Any agitated equipment provided with mechanical means to increase pulp temperature may be used in the conditioning step.

Preferably, the flotation collector added to the dispersed pulp during the conditioning step is an anionic hydroxamate. The quantity of hydroxamate flotation collector required will vary with the crude characteristics and slurry solids and pH.

The conditioned pulp while still hot is transferred to a flotation cell for aeration and flotation. Usually a battery of cells operated in series is used. The flotation cells handle pulps at relatively high solids. The conditioning time is such as to allow liberation of the titanium oxide particles from kaolin and attachment of hydroxamate to the titanium oxide particles. The conditioning time will vary with the crude characteristics, slurry solids, and pH.

During the froth flotation step, the froth product, which is a concentrate of colored titaniferous impurities, is removed from the pulp of purified kaolin clay.

One useful magnetic separation process is disclosed in commonly assigned U.S. Pat. No. 4,781,298 incorporated in its entirety herein by reference. Chemical Additives: One benefit of this invention is that virtually any soluble or insoluble substance or otherwise liquid-mixable chemical may be advantageously homogeneously distributed throughout the mix. Another benefit is an improvement in process efficiency.

Chemical additives may be used throughout the water manufacturing process to improve product quality, improve manufacturing, or reduce cost of the final product. If the functional hydrous kaolin, functional bentonite, or functional mineral is not calcined or otherwise heat treated, the chemical largely or completely remains on, associated with, or evenly distributed among the kaolin, bentonite, or functional mineral. Upon drying, the chemical additive is physically forced to associate with and deposit on the surface of the particle and therefore is found at higher concentration on the particle surface rather than when originally in the vehicle. These particles may now be concentrated to be chemically and/or physically surface modified. Surface modification can result in improved or retarded lipophilicity or hydrophobicity for example. Some unexpected results are that residual chemical additives can have improved functionality when associated with, or evenly distributed among or on the functional hydrous kaolin, functional bentonite, or functional mineral. These chemical additives may advantageously improve the optical properties, sprayability, mixability, deposition, or other properties of an agricultural particle film. Chemical additives may also be added after the water processed product has been dried or while the water processed product is being dried. For example, additives may be added during the pulverization or milling step, or during spray drying.

Preferably, the chemical additive is present at an amount up to about one weight percent of the particle type, but higher concentrations can be used.

Some examples of chemical additives are listed below:

Processing Aids—One non-limiting example of a chemical additive is a processing aid. Certain chemicals are typically used in the processing and manufacture of water purified kaolin, bentonite, or minerals. These processing aids may fit in the described classes of surfactants stated in the examples below, but are not limited to these specific examples. Processing aids are typically used in water processed industrial minerals and rocks to help remove impurities, increase particle brightness, defoam, lower or raise viscosity, coagulate, disperse and suspend particles, modify the iso electric point, zeta potential, or pH (for example surface or internal pH), modify the particle surface to become hydrophobic or hydrophilic, render sprayed bead agglomerates to be hardened to an extent to control film attrition, etc. Examples of such processing aids include but are not limited to acids and bases.

In addition, to their intended use, some processing aids have been shown to have the added benefit of improving the deposition qualities, optical properties, and pesticidal properties of a sprayed particle film. Specifically stated, the processing aids are delivered along with the mineral product to enhance depositions to hydrophobic and hydrophilic surfaces by promoting spray droplet height, film formation and droplet retention to an applied surface. Hence, residual additive chemicals contained with either the dried kaolin product or in the liquid kaolin slurry may be further considered to be deposition aids.

One non-limiting example of a processing aid is a surfactant. While not being bound by any specific description, the broadest definition for the word, surfactant can be simply stated as a word derived from the term "surface active agent". (Amphiphilic molecules that have the unique property of getting absorbed at various interfaces and changing the properties of the interface are called surfactants.) Generally speaking, a surfactant is a substance that may be adsorbed on to a surface, absorbed into a surface, reacted with a surface chemically through covalent or ionic bonds, attracted to a surface by weak hydrogen bonding and Vander Walls forces, or may be forced together through means of external pressure. Under certain instances, there may be no attachment of the surfactant to the surface. Certain surfactants may be extremely limited in utility to specific compounds or classes of substances, while others may be more universal. True to this concept, any chemical compound in the universe may fall into this category. The materials may be organic, inorganic, synthetic, monomeric, polymeric, aliphatic, aromatic, linear, nonlinear and may be found in solid, liquid, gas, or azeotropic state, and may be blends in any combination of these substances. With respect to water, these substances may render a surface hydrophobic or hydrophilic.

Within this concept of a surfactant, materials may be categorized further by their utility including emulsifiers, dispersants, flocculants/coagulants, solvents and the like. For example, an emulsifier is a surface active substance which will provide an intermediate or bridge between two or several substances to produce greater similarity and subsequent homogeneity between them. These surfactant materials generally can be considered cationic, anionic, nonionic, amphoteric, and/or blends of these compounds. A typical example of their use is to suspend oils in water and water in oil. While not being bound by any definition, these substances can also be classified as detergents.

Another categorical example of a surfactant is that of a dispersant. A dispersant in itself may be further categorized by function. In one example, a dispersant is used to modify particles to facilitate easy incorporation into a formulated substance. Note that either the particles or the formulation can range from the molecular to the colloidal to aggregate state and may be solids, liquids, gasses, azeotropes, or blends there of. In yet another example, dispersants are used to separate particles within a formulation to hold them in their finest divided form while prevent them from coming together and reassociating. A specific example may be found in water processed kaolin, where kaolin particles are modified with dispersants to facilitate high solids processing. In this case alkali compounds can be used to neutralize the surface charge, then poly-ionic-polymeric compounds are attached to the surface to provide stearic hindrance. This formulated product compound is then dried and further processed. The resultant, dried kaolin product is considered to be "pre-dispersed" for water based or solvent based systems and is considered to be organically modified and more hydrophilic or lipophilic respectively.

Yet another categorical example of a surfactant is a flocculating agent or coagulant. In this case, the surfactant is added to a system to form large agglomerates of specific substances for ease of separation and removal. Note again, that either the particles or the formulation can range from the molecular level to the colloidal level to aggregate state and may be solids, liquids, gasses, azeotropes, or blends there of. A specific example of their utility may be found in water treatment facilities, where contaminate particles are drawn together using poly-ionic-polymeric compounds to entrap, entangle and concentrate impurities.

Some other general examples of surfactants can be stated as, but are not limited to, the functions, chemistries and blends of the above examples, of buffering agents; pH modifiers; salts; viscosity modifiers; rheological additives; micells; protective colloids; solvents; foaming agents; anti-foaming agents; soaps; chemically, mechanically, radiologically, physically, or thermally modified hydrophiles; chemically, mechanically, radiologically, physically, or thermally modified lipophiles; or formulated ingredient products to deliver desired surfactant properties.

A preferred type of surfactant is ethoxylated alkyl phenols.

Deposition Aids—One non-limiting example of a chemical additive is a deposition aid. In addition to their intended use, chemical additives have been shown to have the added benefit of improving the deposition qualities of a sprayed particle film. The residual chemicals are delivered along with the mineral product to enhance depositions to hydrophobic and hydrophilic surfaces by promoting characteristics such as spray droplet height, film formation, and droplet retention to an applied surface. Hence, residual additive chemicals contained with either the dried kaolin product or in the liquid kaolin slurry may be further considered to be deposition aids. Since calcination and other heat treatment steps may burn off residual chemicals, deposition aids would be added to the mineral after such heat treatment.

In addition to their intended deposition use, some deposition aids have been shown to have the added benefit of improving the processing of particles.

Examples of deposition aids include binders, adhesives, thixotropes, surface tension modifiers, and spreading agents, Delivery vehicle—As a further benefit beyond improving the deposition qualities of particle films, water processing allows for a simple, practical and economical way to modify, formulate and deliver an adjuvant or active ingredient compound to a targeted substrate. Delivered substances in agriculture may be but are not limited to, adjuvants such as spreaders, binders, stickers, drift control agents, penetrators, inhibitors, adhesives, and formulated commercial adjuvants, and active ingredients such as the functional substances in pesticides, plant growth regulators, hormones, disinfectants, nutrients, fungicides, solar protectants, fertilizers, entomopathogens, pheromones, attractants, insect growth regulators, chemosterilants, microbial pest control agents, repellents, viruses, and phagostimulents. Examples of pesticides include insecticides, acaracides, fungicides, bactericides, herbicides, antibiotics, antimicrobials, nemacides, molluscides, and rodenticides.

Some delivered substances may also act as a processing aid, deposition aid, or both.

Blending: The use of water-processed minerals advantageously allows for the even and homogeneous mixture and distribution of additives within the water-processed minerals.

Water-washed minerals can be blended in the dry or wet state after they are processed to attain improved properties for a particle film product. In particular, but not limited to this example, blends of calcined and hydrous minerals can have improved optical, physical, and thermal properties. Minerals mixed in slurry form can attain highly intimate mixing and association and produce homogenous mixtures down to the single particle level. Useful blends comprise calcined minerals and hydrous minerals.

In addition, water-washed mineral alone or the preceding blends of hydrous water-washed mineral and calcined mineral can be used with other minerals such as titanium dioxide.

Examples of such additives include but are not limited to various colors. Such colored particles may be non-reflective. Examples include dark colored pigments such as, but not limited to, natural iron oxides such as yellow limonite, red hematite, brown limonite; black iron oxides such as Pigment Black 10; synthetic iron oxides such as coppers red and ferrite; precipitated red iron oxide; brown iron oxides such as Pigment Brown 6 and brown ocher; synthetic black iron oxides such as Pigment Black 1 and synthetic magnetite; copper-black; chrome-black; zinc magnesium ferrite pigments such as Pigment Brown 11 and mapioc tans; carbon black pigments such as Pigment Black 6 or 7, furnace black, channel black, acetylene black, furnace black, bone black and lampblack; graphite including natural and synthetic graphites such as electrographite or artificial graphite; aniline black such as Pigment black 1; logwood black lakes such as Natural Black 3, Lake Logwood Pigment; yellow sulfur, pigments which directly absorb in the red, blue or green regions or the like.

The pigment ingredient useful for this application may be adsorbed on to a surface, absorbed into a surface, reacted with a surface chemically through covalent or ionic bonds, attracted to a surface by weak hydrogen bonding and Vander Walls forces, or may be forced together through means of external pressure. Other materials may also be attached by use of an accessory ingredient that provides a bridge or link between the two surfaces. Under certain instances, there may be no attachment of the pigment to the particle surface. Certain pigments may be extremely limited in utility to specific particulate compounds or classes of particulate substances, while others may be more universal. Thus, the pigment material may be carried by the insoluble particle to be dislodged and delivered into a liquid based system, or may remain attached to the insoluble particle.

Additional useful pigmenting materials can also include those considered to be "colored", or those pigments which directly absorb in the red, blue or green regions or the like. These materials will generally be reflective of light in the in the visible range. These materials can be either comprised of either organic or inorganic materials or blends there of.

Pigmenting ingredients useful to this invention can also be light colored pigments such as but not limited to titanium dioxide, zinc oxide, hydrous kaolin clay, calcined kaolin clay, and the like. Pigmenting ingredients may also be useful as opacifying agents.

In addition, materials commonly known as effects pigments may be used. Useful effect pigments are platelet-like pigments. The platelets may be made of any substrate material including but not limited to natural mica, synthetic mica, platy glass, platy aluminum oxide, bismuth oxychloride, platy iron oxide, platy graphite, platy silica, bronze, stainless steel, natural pearl, boron nitride, silicon dioxide, copper flake, copper alloy flake, zinc flake, zinc alloy flake, enamel, china clay, porcelain, and mixtures thereof. In a substrate mixture, different materials and/or substrates used in the present invention may have any morphology including platelet, spherical, cubical, acicular, whiskers, or fibrous. Useful glass flakes are disclosed in commonly assigned U.S. Pat. No. 6,045,914 incorporated herein by reference. Boron-free glass may also be used. Useful synthetic mica substrate is disclosed in U.S. Pat. No. 5,741,355 incorporated herein by reference. Preferably, the substrate has a length of about 2.5 microns to about 200 microns and a thickness of about 0.05 micron to about 5 microns.

Typically metal oxide is coated onto the substrate. Examples of useful metal oxides include but not are limited to titanium dioxide including both the anatase and rutile forms, $TiO_x$ where x<2, iron oxide including $Fe_2O_3$ and $Fe_3O_4$, silicon oxide, zinc oxide, zirconium oxide, and mixtures thereof. Multiple layers of different metal oxides may be used.

Natural pearlescent pigments include natural pearlescence and the synthetic pigments include metal oxide-coated mica pigments, metal oxide-coated glass flakes, iron-coated aluminum flakes, and reduced titanium-coated micas. Platy pigments such as the platy titanium dioxide disclosed in commonly assigned U.S. Pat. Nos. 4,192,691 or 5,611,691 may also be used in the present invention.

Further, water processing allows for the controlled blending of different particle sizes and particle morphologies to more efficiently produce a product that is engineered for specific performance criteria. One example is to produce a product containing well-defined, highly resolved combinations of specific particle sizes. Such blends may be referred to bimodal, trimodal, etc. distributions. The benefit of such can be to allow passage of photosynthetic active radiation through a particle film while simultaneously filtering or excluding harmful infrared and ultraviolet radiation. Another example may be the blending of abrasive materials or minerals with minerals of high sorptive capacity and/or that which contain an affinity for lipophylic materials, hydrophilic materials and/or blends there of. Specific uses may be to produce products of higher insecticidal activity such as where the abrasive component penetrates, defeats or otherwise compromises the insect cuticle and the sorptive mineral component causes increased desiccation of the organism.

Surface treatment: The surface of minerals can be treated in either slurry or dry form as noted above. This process usually involves the association of an additive onto the mineral surface resulting in a deposition on the particles in a proportion of 0.1-100% surface coverage on 0.1-100% of the total number of particles. Available surface area of the particles and their relative affinity for the chemical will determine percent coating and quantity of particles covered.

Biocidal Additives: Additional materials may be added to liquid emulsions or liquid slurry products to act as biological inhibiters and retard or prevent the growth of unwanted animal, plant, bacterial, viral, fungal as well as other single celled or colonial microscopic organisms. This group of chemicals is more commonly referred to collectively as biocides.

Calcination: Specific examples of calcined materials include metakaolin, calcined calcium carbonate, calcined talc, calcined kaolin, baked kaolin, fired kaolin, hydrophobic treated heat treated kaolin, calcined bentonites, calcined attapulgite, calcined clays, calcined pyrophyllite, calcined non-crystalline silica, calcined feldspar, calcined sand, calcined chalk, calcined limestone, calcined precipitated calcium carbonate, baked calcium carbonate, calcined diatomaceous earth, calcined barytes, calcined aluminum trihydrate, calcined pyrogenic silica, and calcined titanium dioxide.

In another embodiment, heat treatment involves heating a particulate material at a temperature from about 400° C. to about 1,200° C. for about 10 seconds to about 24 hours. In yet another embodiment, heat treatment involves heating a particulate material at a temperature from about 500° C. to about 1,000° C. for about 10 minutes to about 10 hours. The heat treatment may be carried out in air, in an inert atmosphere or under a vacuum.

Drying: Water-washed minerals may further be processed by heating to dry off water in order to yield products with specific moisture contents. The relative moisture content of the product will determine the ease and rate of re-dispersion and also the integrity of the final product.

Water washed mineral slurries can be spray dried by introducing misted or atomized slurry droplets into a chamber that is heated in order to dry the droplets. This process can be controlled to influence bead size, shape, porosity, strength, hardness, dispersibility, and integrity. Bead performance can be functional in applications due, for example, to their flowability, sorptivity, friability, lack of dusting, moisture content and density. Beads have been shown to exhibit improved friability and softness of film deposition qualities when applied as a particle film. When applied as a re-dispersed slurry, bead integrity in solution may be controlled by chemical additives that inhibit bead breakdown and re-dissociation upon mixing so that the greatest distribution of beads to individual particles may be applied.

Re-dispersion: In addition to producing dry form water-washed end products, non-heat treated materials may be additionally re-dispersed to form slurries and/or combined with other materials to blend and improve the overall product formulation. Similarly, re-dispersion of heat treated minerals, or those materials which have been baked, roasted, fired, calcined or otherwise dried and processed above 400° C., may be reintroduced into a slurry, and may or may not be combined with additional additives to improve suspension, dispersion, retard biological growth and contain or deliver deposition enhancing aids. Typical re-dispersion of a dried product involves the use of high shear mixing, such as a cowles mixer during which time, additional additives or other minerals may be added to improve the final product formulation. Calcined kaolin may be further processed by additional processing methods to reduce product abrasion and increase bulk density. This typically occurs under prolonged, high shear mixing or milling.

Densifying through water addition to dried particles: Wet processed particles that have been dried can be densified through the addition of water or other chemicals. The amount of water or other chemicals that is used is typically less than that used to create a slurry. Optionally, additives may be included. The end result is to create a densified, prilled, granulated, or otherwise bound agglomerate, that results in a higher bulk density, better flowing, or otherwise better performing agricultural particle film product. If desired, higher amounts of water may be used to create pastes.

Pulverization: Spray dried beads or dried mineral slurry cake can be pulverized in order to reduce bead/particle cohesion, and thereby reduce the particle size of the dry-form mineral. Pulverization can also be employed as a mixing process in which additives, or other substances, are co-pulverized and thus intimately blended into the mineral.

Blends: Blends of minerals, hydrous kaolin, calcined kaolin, bentonite, natural calcium carbonate, and synthetic substances may be advantageously used to provide economical and convenient agricultural compositions.

Utility: The horticultural crops to which this invention relate are usually actively growing and fruiting agricultural and ornamental crops and the products thereof, including those selected from the group consisting of fruits, vegetables, trees, flowers, grasses, roots, seeds and landscape and ornamental plants. Particle films can also be applied to picked crops, dormant crops, plants to reduce bark insect infestation, sunburn and cracking, for example, and on the ground under or near plants to improve reflection of useful light onto the plants and control pests. Particle films can be applied to animal surfaces for the purpose of protection from insects and other pests, heat stress, and solar injury.

The substrates or surfaces to which the present invention is applied may be porous and nonporous, homogeneous and heterogeneous, solid, liquid or gaseous, hydrophobic and hydrophilic surfaces that are smooth or rough, and can be purified, oxidized, contaminated or otherwise modified. Examples of surfaces include but are not limited to any natural surface including plant and animal surfaces, or surfaces of man-made structures, or other natural and man-made surfaces. Agricultural substrates include plant substrates or surfaces and animal substrates or surfaces. Plant surfaces include those found on crops, household and ornamental plants, greenhouses, forests with types of surfaces that include leaves, stems, roots, trunks, or fruits, and include soil or other growth mediums, and the like. Examples of animal surfaces include those found on man, birds, arthropods, molluscs, cattle, sheep, horses, chickens, dogs, cats, fish and the like with types of surfaces that include skin, scales, shells, hair, fur, feathers, cuticles, wounds, and the like. Examples of man-made structures include, but is not limited to, those found on walls, floors, shelves, ceilings, stairs and the like in buildings, barns, pens, cages, animal bedding, greenhouses, electrical boxes and the like. Examples of man-made surfaces include metal, alloys, paper, ceramics, glass, concrete, plastic, polystyrene, asphalt, lumber, and the like. Examples of natural surfaces include hides, soil, stone, sand, crude oils, tars, water, ice, wood, lumber, and the like. All of such surfaces shall be collectively referred to as target surfaces.

The uses of the present agricultural composition include but are not limited to crop protectant, pest control and pesticide, growth regulator, delivery vehicle, protective tree paint, animal protectant, heat stress reducer, growth enhancer, agricultural aid, sunburn reducer, frost/freeze preventing agent, nucleating agent, mineral wick, ground-applied light reflectant, and remedy for certain physiological disorders, and coating aid.

The slurry is applied to the target surfaces by spraying, or other suitable means. The particle treatment may be applied as one or more layers. The amount of material applied varies depending upon a number of factors, such as the identity of the substrate, the purpose of the application, and the identity of the particulate material, etc. In any given instance, the amount of material applied can be determined by one of ordinary skill in the art. The amount may be sufficient to form a continuous film, intermittent film, or purposely spotted film over all or a portion of the substrate to which the particle treatment is applied. One or more layers of this dust, slurry, cream or foam may be dusted, sprinkled, sprayed, foamed, brushed on or otherwise applied to the surface. The resultant particulate film residue, whether formed by a dry or slurry application, may result in coatings that are hydrophilic or hydrophobic.

The particle treatment may form a continuous layer. By continuous, it is meant that, where applied, the resultant dry film is continuous (or substantially continuous). For example, in an embodiment where the upper third of a fruit is covered with particulate material mixture in accordance with the present invention, the film covering the upper third of the fruit is continuous or substantially continuous while the bottom two-thirds of the fruit is not covered with the particulate material mixture.

In the continuous film, the maximum average size (average diameter) of pores or non-continuous areas in the particulate film is generally less than about 100 μm. In another embodiment, the maximum average size of openings or non-continuous areas in the particulate film is generally less than about 10 μm. In yet another embodiment, the maximum average size of openings or non-continuous areas in the particulate film is generally less than about 5 μm.

The thickness of the particulate film applied using a dust, slurry, or paste ranges from about 1 μm to about 1 cm. In another embodiment, the thickness of the particulate film ranges from about 3 μm to about 750 μm. In yet another embodiment, the thickness of the particulate film ranges from about 5 μm to about 500 μm.

In one embodiment, the particulate films made in accordance with the present invention do not materially affect the exchange of gases, liquids, solids, or azeotropes on, or with, the target surface. The gases that pass through the particle treatment (or residue from the inventive treatment) are those that are typically exchanged through the target surface and the environment (for example: plant, soil or plant-producing surfaces, mammalian skin, fur or other surfaces). Such gases, vapors or scents include water vapor, carbon dioxide, oxygen, nitrogen, volatile and non-volatile organics, volatile and non-volatile inorganics, fumigants, pheromones and the like. Liquids, solids, and azeotropes include, but are not limited to, such substances as: aqueous-borne sprays, horticultural oils, minerals like sulfur and copper compounds, or blends of liquids, solids, and azeotropes.

In another embodiment, the particulate materials may be used to form a gas, liquid, solid, or azeotrope-impermeable film that restricts the exchange of gases, liquids, solids, or azeotropes on the surface of the substrate. The gases which do not pass through the particle treatment of this embodiment are those which are typically exchanged through the substrates and the environment (for example: plant, soil or plant-producing surfaces, mammalian skin, fur or other surfaces). Such gases, vapors or scents include water vapor, carbon dioxide, oxygen, nitrogen, volatile organics, pheromones, fumigants and the like.

The present agricultural compositions may be used to enhance photosynthesis as disclosed in U.S. Pat. No. 6,110,867, incorporated in its entirety herein by reference. Enhanced photosynthesis has many benefits including increased yields/productivity, e.g., increased fruit size or production (usually measured in weight/acre), improved color, increased soluble solids, e.g. sugar, acidity, etc., reduced plant temperature, increased storage life, increased turgor.

The present agricultural composition may be used in the particle film applications disclosed in U.S. Pat. Nos. 5,908,708; 6,027,740; 6,060,521; 6,069,112; 6,156,327; 6,235,683; 6,464,995; and 6,514,512, all incorporated in their entirety herein by reference.

Since gases such as carbon dioxide enter plants through the plants' stomates and the aperture of a stomate varies depending upon the plant, one skilled in the art having selected a horticultural crop would select a composition particle size and amount of application for that selected crop to achieve the desired result. The present agricultural composition may be applied from 20 up to about 5,000 micrograms of particulate material per cm$^2$ of surface for particles having specific density of around 2-3 g/cm$^3$, more typically from about 100 up to about 3,000, and preferably from about 100 up to about 500. In addition, environmental conditions such as wind, temperature, contaminants, pollution, and rain may reduce coverage of the particulate material and therefore, multiple applications may be desirable.

The present compositions may include a spreading agent. Upon applying the present composition including a spreading agent to a substrate, the spreading agent increases the substrate area covered by the composition.

The present compositions may also include a volumization agent. Upon applying the present composition including a volumization agent to a substrate, the volumization agent increases the separation of a given mass of particles.

Non-agricultural uses for the present invention include as a masking spray for painting, temporary coating, acoustic interference and disruption, infrared radiation dissipation, and camouflaging military vehicles and equipment.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

Analytical Tests:

Crystalline Silica: The test for the amount of crystalline silica is the NIOSH Manual of Analytical Methods, Crystalline Silica by xrd, Method 7500, Issue 3, Fourth Edition (Jan. 15, 1998).

1. Obtain a qualitative X-ray diffraction scan (e.g., 10 to 8020) of the area air sample (or bulk settled dust) to determine the presence of free or crystalline silica polymorphs and interferences. The expected diffraction peaks are:

Peak (2-Theta Degrees)

| Mineral | Primary | Secondary | Tertiary |
|---|---|---|---|
| Crystalline silica | 26.66 | 20.85 | 50.16 |
| Cristobalite | 21.93 | 36.11 | 31.46 |
| Tridymite | 21.62 | 20.50 | 23.28 |
| Silver | 38.12 | 44.28 | 77.47 |

2. Perform the following for each sample, working standard, and blank filter. (a) Mount the reference specimen. Determine the net intensity Ir of the reference specimen before and after each filter is scanned. Use a diffraction peak of high intensity that can be rapidly but reproducibly ($S_r$<0.01) measured. (b) Mount the sample, working standard, or blank filter. Measure the diffraction peak area for each silica polymorph. Scan times must be long, e.g., 15 minutes Longer scan times will lower the limit of detection. (c) Measure the background on each side of the peak for one-half the time used for peak scanning. The sum of these two counts is the average background. Determine the position of the background for each sample. (d) Calculate the net intensity $I_x$. This is the difference between the peak integrated count and the total background count. (e) Calculate and record the normalized intensity $\hat{I}_x$ for each peak: $\hat{I}_x = (I_x/I_r)N$. Select a convenient normalization scale factor, N, which is approximately equivalent to the net count for the reference specimen peak, and use this value of N for all analyses. Normalizing to the reference specimen intensity compensates for long-term drift in X-ray tube intensity. If intensity measurements are stable, the reference specimen may be run less frequently and the net intensities should be normalized to the most recently measured reference intensity. (f) Determine the normalized count $\hat{I}_{Ag}$ of an interference-free silver peak on the sample filter following the same procedure. Use a short scan time for the silver peak (e.g., 5% of scan time for analyte peaks) throughout the method. (g) Field blanks may be analyzed by scanning the 2-theta range used for the analyte and silver peaks to verify that contamination of the filters has not occurred. The analyte peak should be absent. The normalized intensity of the silver peak should match that of the media blank. Each laboratory should determine the specifics of field blank use for its application. When contamination does occur, the reason should be investigated and appropriate action taken. In practice, contamination of field blanks is extremely rare and usually is not consistent across filters. The analysis of blanks may be abbreviated if experience indicates that contamination is not likely with current field and laboratory operations; however, occasional confirmation of non-contamination is prudent.

3. Calculate the concentration of crystalline silica C(mg/m$^3$) in the air volume sampled: $C=[\hat{I}_x \cdot f(t)-b]/(m \cdot V)$ in mg/m$^3$ where $\hat{I}_x$ is the normalized intensity for the sample peak, b is the intercept of the calibration graph, m is the slope of the calibration graph in counts/microgram, f(t) is $-R \ln T(1-T^R)$ (an absorption coefficient factor), R is $\sin\theta_{Ag}/\sin\theta_x$, T is $\hat{I}_{Ag}$/average $I°_{Ag}$ average (sample transmittance), $\hat{I}_{Ag}$ is the normalized silver peak intensity from the sample, and $I°_{Ag}$ is the normalized silver peak intensity from media blanks (an average of six values).

The available surface area of a particle, percent coating and relative particle affinity for chemical species may be determined through surface area analysis, oil absorption determination and other physical means. Some example test methods are as follows.

Surface Area: Surface area (ASTM D 3663-78) is determined by measuring the volume of nitrogen gas adsorbed by the sample at several pressure levels. The B.E.T (1) equation in its linear form is then used to determine the volume of adsorbed gas equivalent to a monomolecular layer. This is done by fitting a straight line to three relative pressure points (0.08, 0.014 and 0.30) on the linear portion of the isotherm, and determining the slope and intercept corresponding to the line of least squares. From the slope and effective cross-sectional areas of a single nitrogen molecule (0.162 sq. meters), the surface area of the sample is calculated. This method can be used to determine the total surface area of materials that have Type II of Type IV nitrogen adsorption isotherms, and whose physical geometry and inert chemical nature are changed by the outgassing procedure. The specific surface area must be at least 1 sq. meter per gram. If this method is applied to zeolitic materials, the reported surface area is a measure of nitrogen uptake by condensation in the zeolite pores as well as adsorption on the surface. Allocation of gas between pores and surface cannot be done by the B.E.T. method. The testing is carried out by attaching a clean, dry tube to the port of an outgassing station. The tube must have a matching, marked stopper that is either fritted which remains on the tube when it is attached to the port or, a separate rubber stopper which is removed. The tube is evacuated while heating to 250 degrees centigrade, with maintenance of heat for 15 minutes. The tube is then cooled and backfilled with helium to ambient pressure or slightly above. The tube is then removed from the outgassing station and capped immediately. The tube and stopper are weighed while it is filled with the helium. This tare weight is then used for subsequent runs as long as the tube and stopper do not change weight due to tear or chipping. A sample of not less than 10 sq. meters total surface area is pulverized or broken to enable placement into the tube. If the surface area is expected to be 50 sq. meters per gram or higher, 0.3 g of sample is used; If the specific surface area is expected to be below 50 sq. meters per gram, the calculation W=15/s (where S is the expected specific surface area in sq. meters per gram) is used to approximate the sample weight. The appropriate weight of the sample is transferred onto a piece of weighing paper on a top loading balance. The sample is then transferred to a clean, tarred sample tube with the aid of a funnel, removing any sample on the neck of the sample tube with a pipe cleaner. Except for heat sensitive materials, outgassing is normally performed at 250 degrees centigrade for at least 4 hours. The outgassed samples are left attached to the ports until it is time to perform the surface area measurement. The true sample weight is then determined by first being certain that the sample tube has cooled to room temperature. The tube is then removed from the outgassing station and stoppered immediately. Unless otherwise indicated, surface area is determined from relative pressure points at 0.08, 0.14, 0.20. The sample weight is calculated as sample weight=final sample weight−original sample weight.

Particle Size: Particle size and particle size distribution as used herein are measured with a Micromeritics Sedigraph 5100 Particle Size Analyzer. Measurements are recorded in deionized water for hydrophilic particles. Dispersions are prepared by weighing 4 grams of dry sample into a plastic beaker, adding dispersant and diluting to the 80 ml mark with deionized water. The slurries are then stirred and set in an ultrasonic bath for 290 seconds. Typically, for kaolin 0.5% tetrasodium pyrophosphate is used as a dispersant; with calcium carbonate 1.0% Calgon T is used. Typical densities for the various powders are programmed into the sedigraph, for example, 2.58 g/ml for kaolin. The sample cells are filled with the sample slurries and the X-rays are recorded and converted to particle size distribution curves by the Stokes equation. The median particle size is determined at the 50% level.

In the examples, "ppt" means pounds of reagent per ton of clay solids.

The equivalent spherical diameter for particles was measured with a Micromeritics Sedigraph 5000 particle size analyzer.

The percent titanium dioxide was determined by x-ray fluorescence (xrf).

The TAPPI brightness was measured according to TAPPI Standard T-646 OS75 on a Technidyne S-4 Brightness Tester.

Comparative A:

Serina is a commercially available agricultural composition as reported in Table 1 above.

INVENTIVE EXAMPLE 1

Kaolin having $TiO_2$-equivalent at greater than one percent was water processed to remove crystalline silica, iron contamination, and base metal oxides. The resulting hydrous kaolin was substantially free of crystalline silica and the $TiO_2$-equivalent content was less than one percent. The kaolin surface was chemically modified with a chemical additive. The chemical additive used was an alkali and an anionic polymeric surfactant in an amount of less than one weight percent. The additive used was a processing aid and not fully functional as a deposition aid.

The composition was spray dried to form beads. The chemical additive was uniformly distributed on, associated with, or evenly distributed among the hydrous kaolin. The kaolin had a crystalline silica=<0.2% (non detectable); +325 Residue=<0.01%, Einlehner=<5; $TiO_2$=0.61% (The kaolin source had a $TiO_2$-equivalent of between 1.0 and 2.0 weight percent.); GE Brightness=92; and average PSD=0.4 μm. An agricultural composition is made from this kaolin and is applied to a substrate in an amount greater than or equal to about an average of 20 micrograms per square centimeter on the substrate.

INVENTIVE EXAMPLE 2

Inventive Example 1 was repeated except that the chemical additives also included a defoamer and a non-ionic detergent which were added prior to spray drying in an amount of less than one weight percent.

INVENTIVE EXAMPLE 3

Inventive Example 2 was repeated except that a cationic polymeric coagulant was added in an amount of less than one weight percent.

INVENTIVE EXAMPLE 4

Inventive Example 1, 2, or 3 is repeated except that processing is halted before spray drying and the product is slurried to form a concentrated product.

INVENTIVE EXAMPLE 5

Inventive Example 4 is repeated except that a biocide is added at the end.

INVENTIVE EXAMPLES 6-8

Each of Inventive Examples 1-3 is repeated except that calcined kaolin is blended with the hydrous kaolin in an amount of 20-50 weight percent based on the solids content. Thus, the resulting blend has 20-50 weight percent calcined kaolin and 50-80 weight percent of the Inventive Example 1 product.

INVENTIVE EXAMPLE 9

Inventive Example 1, 2, or 3 is repeated except that an active ingredient consisting of copper fungicide is added before drying. The copper fungicide is uniformly distributed on, associated with, or evenly among the hydrous kaolin.

INVENTIVE EXAMPLE 10

A deposition enhancing aid is added to a precipitated or ground calcium carbonate during manufacturing.

INVENTIVE EXAMPLE 11

Inventive Example 1 above is repeated except that a chemical additive is used during the spray drying process.

INVENTIVE EXAMPLE 12

Inventive Example 1 above is repeated except that prior to or after spray drying, a non-water processed particle is mixed in.

INVENTIVE EXAMPLES 13-24

Each of Inventive Examples 1-12 is used as an end-product.

INVENTIVE EXAMPLE 25

Figure 2:
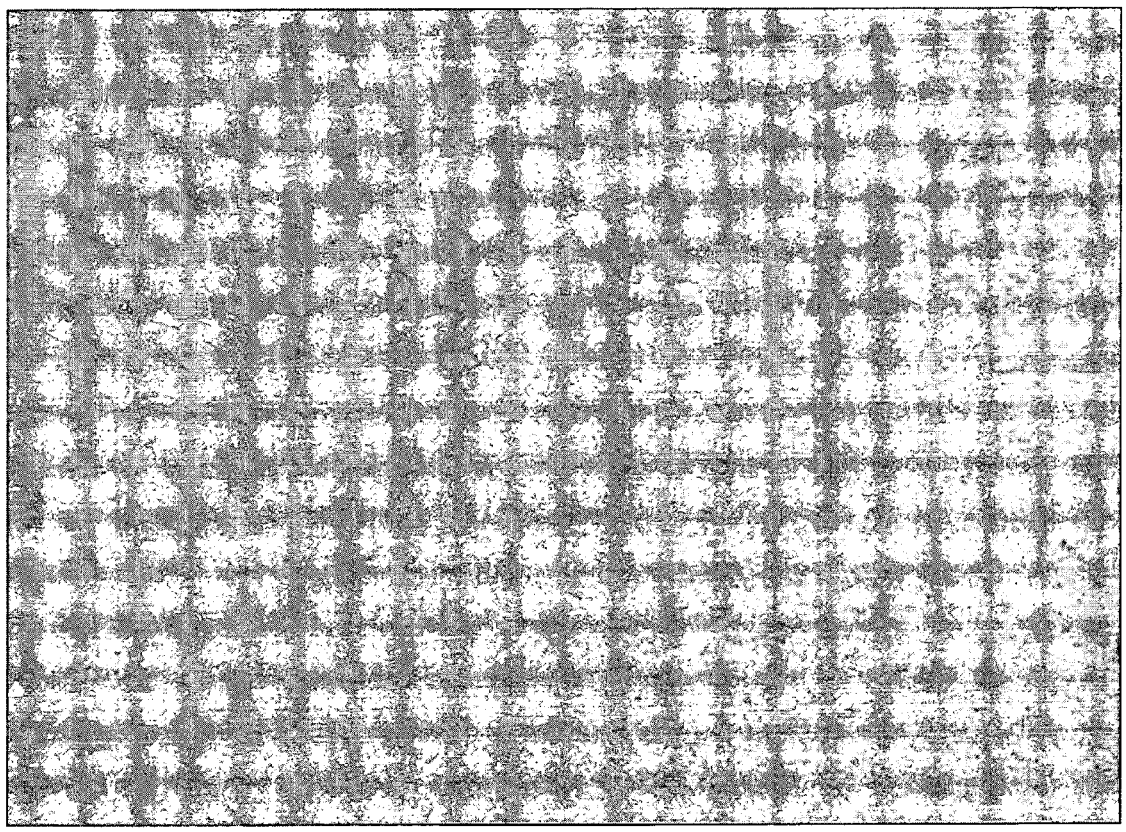
FIG. 2 shows an example of the present agricultural composition.

Inventive Example 1 above was repeated except that the anionic polymer was replaced by a nonionic surfactant and a defoamer. FIG. 2 shows the resulting product wherein the chemical additives are uniformly distributed among or on the hydrous kaolin. This is in contrast to FIG. 1 showing SURROUND® WP crop protectant.

INVENTIVE EXAMPLE 26

The product of Inventive Example 1 above is blended with water processed calcined kaolin at a 50:50 ratio. A spreading agent and volumization agent are added to the blend. The resulting blend has unexpectedly good rainfastness and optical properties.

INVENTIVE EXAMPLE 27

Inventive Example 1 is repeated except that calcined kaolin is used instead of hydrous kaolin.

INVENTIVE EXAMPLE 28 AND COMPARATIVE B AND C

A water processed hydrous kaolin was prepared and a liquid and one dry-form additive were added into the kaolin slurry. The additives were two different deposition aids. The slurry was then dried and milled to form Inventive Example 28.

Another water processed hydrous kaolin was prepared. Two additives were added in dry form to the dry kaolin and then dry-milled together to form Comparative B.

To form Comparative C, Comparative B was repeated except that the additives were tumbled in and not milled.

Each of the resulting samples was slurried and then passed through a series of screens: 20, 20, 40, 60, 100, 140, 200, and 325 mesh. The screens were rinsed with water and the residue in percent by weight of each screen was collected, dried, and weighed. The residue results by screen size are as follows where NM means not measured.

| Sieve No. | Inventive Example 28 | Comparative B | Comparative C |
|---|---|---|---|
| 20 | NM | 3.83% | 0.43% |
| 30 | NM | 2.66 | 0.13 |
| 40 | NM | 1.52% | 0.04% |
| 60 | 0.0 | 2.48% | 0.04% |
| 100 | 0.0 | 3.08% | 0.10% |
| 140 | 0.0 | 0.49% | 0.17% |
| 200 | 0.0 | 0.42% | 0.01% |
| 325 | 0.0 | 0.22% | 0.20% |
| Total Residue | 0.0 | 14.7% | 1.12% |

The results clearly show that wet processing of the additives as in Inventive Example 28 gave a uniform distribution of the additives as seen by the result that no measurable residue of additives and/or kaolin was in the screens. In sharp contrast, Comparatives B and C both showed significant screen residue indicating a lack of uniformity in the slurries. Moreover, Comparative B exhibited significant residue even though the sample was dry-milled before slurrying. Comparative B actually showed worse residue versus the non-milled Comparative C.

The products of Inventive Example 28 and Comparative B were also sprayed onto clear polyethylene over a black surface as shown in FIG. 3. This polyethylene was a hydrophobic surface that resembles an agricultural surface to which it is difficult to apply chemical additives. As shown in FIG. 3, Inventive Example 28 showed excellent film formation and few or no specks of undissolved additives while Comparative B showed poor film formation and specks of undissolved additives and kaolin due to inefficient action of the additive when sprayed.

INVENTIVE EXAMPLES 29 AND 30 AND COMPARATIVE D

A water processed hydrous kaolin in beaded form similar to the product of Inventive Example 1 above except that the kaolin was slightly coarser and not as bright was used for Inventive Example 29. A water processed hydrous kaolin that was not beaded was used for Inventive Example 30. Comparative D was an air floated hydrous kaolin that was not beaded (sold by DBK Co., now Imerys).

30 grams of the three different kaolins were put into 100 cc graduated cylinders. Volume readings were taken immediately and after one and five minutes of tamping. The resulting volumes and bulk densities are below:

| Time | Inventive Example 29 Volume (cc) | Inventive Example 30 Volume(cc) | Comparative D Volume(cc) |
|---|---|---|---|
| Initial | 43 | Approximately 102 | 77 |
| One minute | 30 | 73 | 55 |
| Five minutes | 30 | 64 | 46 |

-continued

| Time | Inventive Example 29 Bulk Density (g/cc) | Inventive Example 30 Bulk Density (g/cc) | Comparative D Bulk Density (g/cc) |
|---|---|---|---|
| Initial | 0.70 | 0.30 | 0.39 |
| One minute | 1.0 | 0.41 | 0.55 |
| Five minutes | 1.0 | 0.47 | 0.65 |

Thus, the same mass of Inventive Example 29 took up much less volume due to a higher bulk density than the others as shown in FIG. 4 where IE 29 stands for Inventive Example 29, IE 30 stands for Inventive Example 30, and Comp D stands for Comparative D.

INVENTIVE EXAMPLE 31

Figures 5, 5A, 5B:
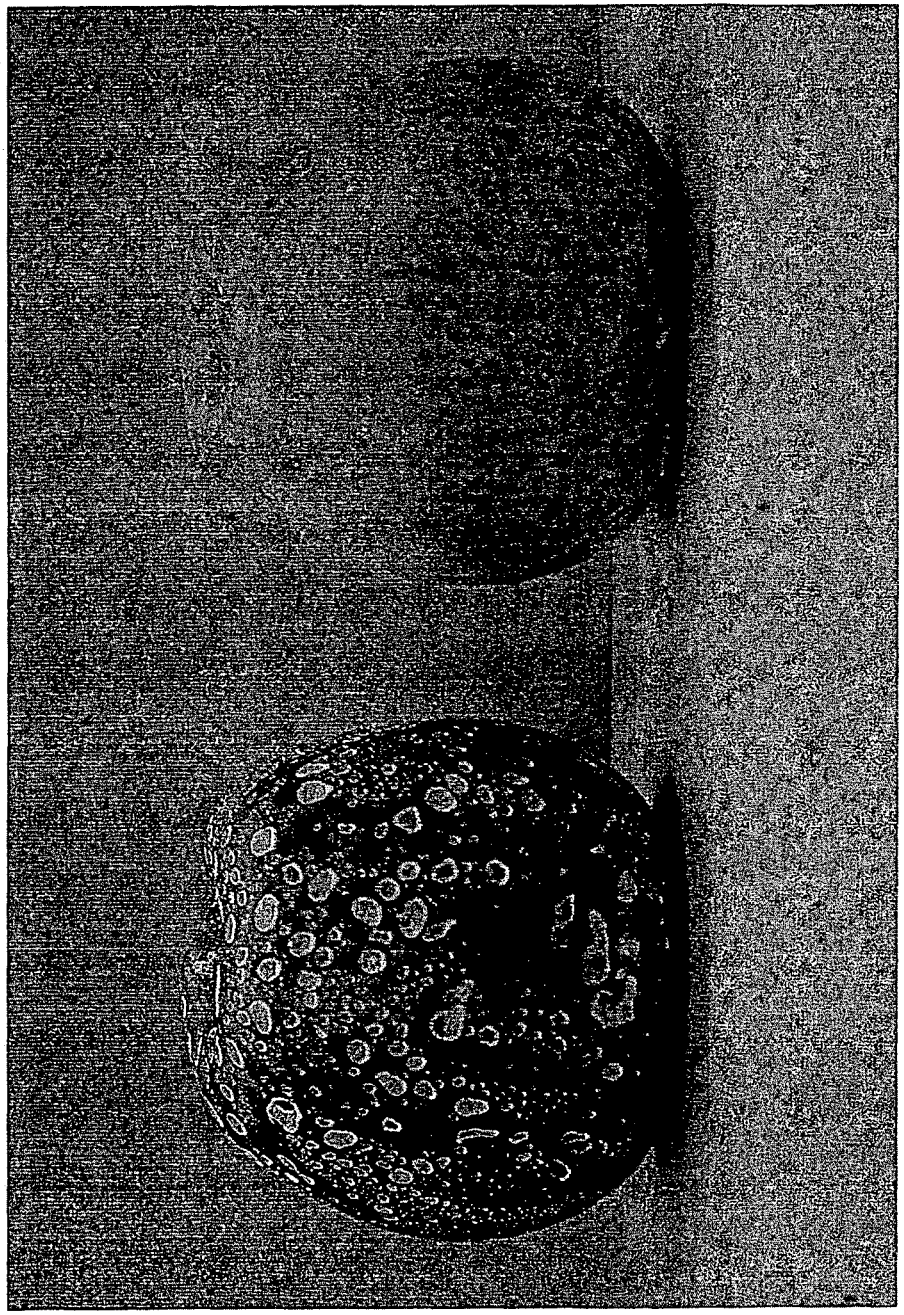
FIG. 5 shows other examples of the present agricultural composition.

Inventive Example 31 was prepared using the water processed hydrous kaolin of Inventive Example 1 above and then, a chemical additive was added at the pulverizer and was functional as a deposition aid. The product of Inventive Example 1 was applied to an apple and is shown on the left side of FIG. 5. The product of Inventive Example 31 was applied to another apple and is shown on the right side of FIG. 5. The benefit of adding a chemical additive at the pulverizer is clearly shown in the intimate blend on the apple on the right side of FIG. 5.

INVENTIVE EXAMPLE 32

Kaolin was purified via water processing to remove crystalline silica and other contaminants and was treated with an acidic chemical additive to reduce the pH. The chemical additive was uniformly distributed on, associated with, or evenly distributed among the hydrous kaolin. The composition was dried and milled. The kaolin had crystalline silica=<0.2% (non detectable); +325 Residue=<0.015%, Einlehner=<10, $TiO_2$=1.6%, GE Brightness=85-87; and average PSD=0.6 μm. An agricultural composition is made from this kaolin and is applied to a substrate in an amount greater than or equal to about an average of 20 micrograms per square centimeter on the substrate.

INVENTIVE EXAMPLE 33 AND COMPARATIVES E AND F

Inventive Example 33 was prepared like Inventive Example 32 except that it was made in a finer average particle size distribution—(0.4) μm.

The graph in FIG. 6 shows the products of Inventive Examples 32 and 33 compared with Comparatives E (Snow brand kaolin described in Table 2 above) and F (Sunguard brand kaolin described in Table 2 above).

It is advantageous to reflect infrared (IR) light as this can reduce the heat load on a surface. The four samples were applied in an aqueous spray to a glass slide at varying mass levels and the amount of IR reflectance was measured for all mass levels. The data show that the products of Inventive Examples 32 and 33 have much higher IR light reflection compared with Comparatives E and F.

What is claimed is:

1. An agricultural substrate having an agricultural particle film thereon wherein said agricultural particle film comprises functional particles that are substantially free of crystalline silica and selected from the group consisting of water-processed hydrous kaolin or water-processed bentonite, and said agricultural particle film is a crop protectant and is present in an amount greater than or equal to about an average of 20 micrograms per square centimeter on said substrate.

2. The agricultural substrate of claim 1 wherein said agricultural particle film additionally comprises a chemical additive.

3. The agricultural substrate of claim 2 wherein said chemical additive is uniformly distributed among or on the functional particles.

4. The agricultural substrate of claim 1 wherein said functional particles are in beaded or agglomerated form.

5. The agricultural substrate of claim 1 wherein said agricultural particle film additionally comprises a pest control agent.

6. The agricultural substrate of claim 1 wherein said agricultural particle film comprises a functional amount of water-processed hydrous kaolin, wherein the agricultural particle film has a $TiO_2$ content less than one percent by weight.

7. An agricultural substrate having an agricultural particle film thereon wherein said agricultural particle film comprises (a) functional particles selected from the group consisting of water-processed hydrous kaolin and water-processed bentonite and (b) a chemical additive that is uniformly distributed among or on said functional particles, and said agricultural particle film is a crop protectant and is present at greater than or equal to about an average of 20 micrograms per square centimeter on said substrate.

8. The agricultural substrate of claim 7 wherein said functional particles (a) are in beaded or agglomerated form.

9. The agricultural substrate of claim 7 wherein said agricultural particle film additionally comprises a pest control agent.

10. The agricultural substrate of claim 7 wherein the agricultural particle film additionally comprises a second chemical additive.

11. The agricultural substrate of claim 1 wherein said functional particles comprise water-processed hydrous kaolin.

12. The agricultural substrate of claim 1 wherein said functional particles comprise water-processed bentonite.

13. The agricultural substrate of claim 1 wherein said agricultural particle film is present in an amount between 100 and 3000 micrograms per square centimeter average on said substrate.

14. The agricultural substrate of claim 1 wherein said functional particles have a GE Brightness equal to or greater than 85 and an average particle size less than 2 microns.

15. The agricultural substrate of claim 1 wherein said agricultural particle film further comprises a surfactant, a dispersant, or both.

16. The agricultural substrate of claim 15 wherein said surfactant comprises an ethoxylated alkyl phenol.

17. The agricultural substrate of claim 1 wherein said agricultural particle film further comprises a flocculating agent or coagulant.

18. The agricultural substrate of claim 1 wherein said agricultural particle film further comprises a spreading agent and a volumization agent.

19. The agricultural substrate of claim 1 wherein said agricultural particle film is present in an amount between 100 and 3000 micrograms per square centimeter average on said substrate and wherein said functional particles comprise water-processed hydrous kaolin having a GE brightness of at least 85.

20. An agricultural substrate having an agricultural particle film thereon wherein said agricultural particle film comprises functional particles that contain less than 0.25 by weight of crystalline silica, wherein said functional particles are selected from the group consisting of water-processed hydrous kaolin, water-processed natural calcium carbonate, water-processed bentonite, or mixture thereof, and said agricultural particle film is a crop protectant and is present in an amount from about 100 up to about 3,000 micrograms per square centimeter on said substrate.

21. The agricultural substrate of claim 20 wherein said agricultural particle film is free of crystalline silica.

22. The agricultural substrate of claim 21 wherein said functional particles comprise water-processed hydrous kaolin having a GE brightness of at least 92.

23. The agricultural substrate of claim 20 wherein said functional particles are hydrous kaolin having a GE brightness of at least 85.

24. The agricultural substrate of claim 20 wherein said functional particles are water-processed bentonite having a GE brightness of at least 85.

25. The agricultural substrate of claim 20 wherein said agricultural particle film is present in an amount between 100 and 3000 micrograms per square centimeter average on said substrate and wherein said functional particles are water-processed natural calcium carbonate which is substantially free of crystalline silica.

26. The agricultural substrate of claim 7 wherein said chemical additive is applied to the particles during the step of water processing the particles.

27. The agricultural substrate of claim 7 wherein said chemical additive improves the optical properties of said agricultural particle film.

28. The agricultural substrate of claim 1 wherein the functional particles are water-processed hydrous kaolin that has been delaminated.

29. The agricultural substrate of claim 1 wherein the functional particles are water-processed bentonite that has been delaminated.

30. The agricultural substrate of claim 1 wherein the functional particles have a median particle size equal to or less than about 0.4 micron.

31. The agricultural substrate of claim 20 wherein the functional particles are water-processed natural calcium carbonate which further comprises dolomite, said functional particles having a median particle size equal to or less than about 0.4 micron.

32. The agricultural substrate of claim 31 wherein the functional particles are substantially free of crystalline silica.

33. The agricultural substrate of claim 20 wherein the functional particles comprise a surfactant, said surfactant having been added to a slurry of said functional particles which were dried so the surfactant is physically forced to associate with and deposit on the surface of the particle.

34. The agricultural substrate of claim 20 wherein the functional particles have a specific surface area of 50 square meters per gram or higher.

35. The agricultural substrate of claim 20 wherein the functional particles have a bimodal particle size distribution to allow passage of photosynthetic active radiation while filtering and excluding harmful infrared and ultraviolet radiation.

36. The agricultural substrate of claim 20 wherein the functional particles have a trimodal particle size distribution.

37. The agricultural substrate of claim 20 wherein the functional particles are water-processed natural calcium carbonate and wherein the functional particles have a bimodal or trimodal particle size distribution to allow passage of photosynthetic active radiation while filtering and excluding harmful infrared and ultraviolet radiation.

* * * * *